(12) United States Patent
Wurster et al.

(10) Patent No.: US 8,455,529 B2
(45) Date of Patent: *Jun. 4, 2013

(54) KINASE INHIBITORS

(75) Inventors: Julie A. Wurster, Irvine, CA (US); Richard C. Yee, Tustin, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/229,043

(22) Filed: Sep. 9, 2011

(65) Prior Publication Data

US 2011/0319460 A1 Dec. 29, 2011

Related U.S. Application Data

(63) Continuation of application No. 12/377,098, filed as application No. PCT/US2007/075669 on Aug. 10, 2007, now Pat. No. 8,034,957.

(60) Provisional application No. 60/822,105, filed on Aug. 11, 2006.

(51) Int. Cl.
  *A61K 31/4178* (2006.01)
  *A61K 31/4155* (2006.01)
  *C07D 403/02* (2006.01)

(52) U.S. Cl.
  USPC ...... 514/397; 514/406; 548/312.1; 548/364.7

(58) Field of Classification Search
  USPC ............... 514/397, 406; 548/312.1, 364.7
  See application file for complete search history.

(56) References Cited

U.S. PATENT DOCUMENTS

| 5,792,783 | A  | 8/1998  | Tang et al. |
| 5,834,504 | A  | 11/1998 | Tang et al. |
| 5,883,113 | A  | 3/1999  | Tang et al. |
| 5,883,116 | A  | 3/1999  | Tang et al. |
| 5,886,020 | A  | 3/1999  | Tang et al. |
| 6,541,504 | B1 | 4/2003  | Andrews et al. |
| 6,559,173 | B1 | 5/2003  | Andrews et al. |
| 6,699,863 | B1 | 3/2004  | Andrews et al. |
| 6,747,025 | B1 | 6/2004  | Andrews et al. |
| 6,765,012 | B2 | 7/2004  | Andrews et al. |
| 7,005,444 | B2 | 2/2006  | Andrews et al. |
| 7,015,220 | B2 | 3/2006  | Andrews et al. |
| 7,060,844 | B2 | 6/2006  | Andrews et al. |

FOREIGN PATENT DOCUMENTS

| WO | WO2006/052936 | 5/2006 |
| WO | WO 2007/008895 | 1/2007 |
| WO | WO2007/008985 | 1/2007 |

OTHER PUBLICATIONS

Bolen, 1993, Oncogen 8: 2025-2031.
Golub, et al., Science, vol. 286, pp. 531-537, 1999.
Lala, et al., Cancer and Metastasis Reviews (1998, 17(1), pp. 91-106.
Plowman, et al., 1994, DN&P 7(6): 334-339.

*Primary Examiner* — Samantha Shterengarts
(74) *Attorney, Agent, or Firm* — Krishna G. Banerjee

(57) ABSTRACT

The present invention relates to organic molecules capable of modulating tyrosine kinase signal transduction in order to regulate, modulate and/or inhibit abnormal cell proliferation.

6 Claims, No Drawings

KINASE INHIBITORS

CROSS-REFERENCE TO RELATED APPLICATION

This application is a continuation of Ser. No. 12/377,098, filed Feb. 10, 2009, now U.S. Pat. No. 8,034,957 which is a §371 National Stage of PCT/US2007/075669, filed Aug. 10, 2007, which claims the benefit of U.S. Provisional Application Ser. No. 60/822,105, filed Aug. 11, 2006, each of which is hereby incorporated by reference herein in its entirety.

BACKGROUND OF THE INVENTION

1. Field of the Invention

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

2. Description of the Related Art

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The RTKs comprise a large family of transmembrane receptors with diverse biological activities. The intrinsic function of RTKs is activated upon ligand binding, which results in phosphorylation of the receptor and multiple cellular substrates, and subsequently in a variety of cellular responses.

At present, at least nineteen (19) distinct RTK subfamilies have been identified. One RTK subfamily, designated the HER subfamily, is believed to be comprised of EGFR, HER2, HER3 and HER4. Ligands to the HER subfamily of receptors include epithelial growth factor (EGF), TGF-$\alpha$, amphiregulin, HB-EGF, betacellulin and heregulin.

A second family of RTKs, designated the insulin subfamily, is comprised of the INS-R, the IGF-1R and the IR-R. A third family, the "PDGF" subfamily includes the PDGF $\alpha$ and $\beta$ receptors, CSFIR, c-kit and FLK-II. Another subfamily of RTKs, identified as the FLK family, is believed to be comprised of the Kinase insert Domain-Receptor fetal liver kinase-1 (KDR/FLK-1), the fetal liver kinase 4 (FLK-4) and the fms-like tyrosine kinase 1 (flt-1). Each of these receptors was initially believed to be receptors for hematopoietic growth factors. Two other subfamilies of RTKs have been designated as the FGF receptor family (FGFR1, FGFR2, FGFR3 and FGFR4) and the Met subfamily (c-met and Ron).

Because of the similarities between the PDGF and FLK subfamilies, the two subfamilies are often considered together. The known RTK subfamilies are identified in Plowman et al, 1994, DN&P 7(6): 334-339, which is incorporated herein by reference.

The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and includes Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, Oncogene 8: 2025-2031, which is incorporated herein by reference.

Many of the tyrosine kinases, whether an RTK or non-receptor tyrosine kinase, have been found to be involved in cellular signaling pathways leading to cellular signal cascades leading to pathogenic conditions, including cancer, psoriasis and hyper immune response.

In view of the surmised importance of PTKs to the control, regulation and modulation of cell proliferation the diseases and disorders associated with abnormal cell proliferation, many attempts have been made to identify receptor and non-receptor tyrosine kinase "inhibitors" using a variety of approaches, including the use of mutant ligands soluble receptors and antibodies RNA ligands and tyrosine kinase inhibitors.

More recently, attempts have been made to identify small molecules which act as tyrosine kinase inhibitors. For example, bis monocyclic, bicyclic or heterocyclic aryl compounds, vinylene-azaindole derivatives and 1-cyclopropyl-4- pyridyl-quinolones have been described generally as tyrosine kinase inhibitors. Styryl compounds, styryl-substituted pyridyl compounds certain quinazoline derivatives selenoindoles and selenides, tricyclic polyhydroxylic compounds and benzylphosphonic acid compounds have been described as compounds for use as tyrosine kinase inhibitors for use in the treatment of cancer.

The identification of effective small compounds which specifically inhibit signal transduction by modulating the activity of receptor and non-receptor tyrosine kinases to regulate and modulate abnormal or inappropriate cell proliferation is therefore desirable and one object of this invention.

Finally, certain small compounds are disclosed in U.S. Pat. Nos. 5,792,783; 5,834,504; 5,883,113; 5,883,116 and 5,886,020 as useful for the treatment of diseases related to unregulated TKS transduction. See also, U.S. Pat. Nos. 6,541,504; 6,559,173; 6,765,012; 6,747,025; 6,699,863; 7,005,444; 7,015,220 and 7,060,844. These patents are hereby incorporated by reference in its entirety for the purpose of disclosing starting materials and methods for the preparation thereof, screens and assays to determine a claimed compound's ability to modulate, regulate and/or inhibit cell proliferation, indications which are treatable with said compounds, formulations and routes of administration, effective dosages, etc.

BRIEF SUMMARY OF THE INVENTION

The present invention relates to organic molecules capable of modulating, regulating and/or inhibiting tyrosine kinase signal transduction. Such compounds are useful for the treatment of diseases related to unregulated TKS transduction, including cell proliferative diseases such as cancer, atherosclerosis, restenosis, metabolic diseases such as diabetes, inflammatory diseases such as psoriasis and chronic obstructive pulmonary disease, vascular proliferative disorders such as diabetic retinopathy, age-related macular degeneration and retinopathy of prematurity, autoimmune diseases and transplant rejection.

DETAILED DESCRIPTION OF THE INVENTION

Compounds of the general formulas I and II below are useful as kinase inhibitors. As such compounds of formula I will be useful for treating diseases related to unregulated tyrosine kinase signal transduction, for example, cancer, blood vessel proliferative disorders, fibrotic disorders, and neurodegenerative diseases. In particular compounds of the present invention are useful for the treatment of mesangial cell proliferative disorders and metabolic diseases, diabetic retinopathy, age-related macular degeneration, retinopathy of prematurity, arthritis, restenosis, hepatic cirrhosis, atherosclerosis, psoriasis, diabetes mellitus, wound healing, inflammation and neurodegenerative diseases.

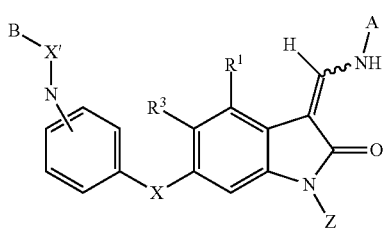

I

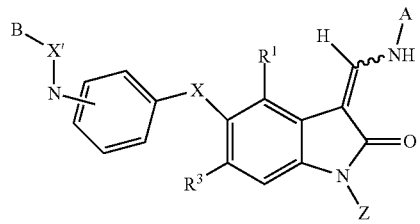

II

Wherein substituents listed are illustrated but not limited to the illustrative list set forth below:

wherein X is selected from the group consisting of C=O, C=S, $CR^4R^5$, O, S, NH, and $NR^4$;

Z is selected from the group consisting of hydrogen, $C_1$ to $C_8$ alkyl, phenyl, hydroxymethyl, —$CH_2$—N(—$CH_2CH_2WCH_2CH_2$—), $COCH_3$, $CH_2CH_2OH$, and $CH_2CH_2CH_2OH$;

W is selected from the group consisting of O, S, $CH_2$ and $NCH_3$;

$R^1$ is selected from the group consisting of hydrogen and $CH_3$;

$R^3$ is selected from the group consisting of hydrogen, $C_1$ to $C_8$ alkyl, phenyl, hydroxymethyl, $COCH_3$, $CH_2CH_2OH$, $CH_2CH_2CH_2OH$ and $[C(R^2)_2]_cN(R^2)_2$, wherein $R^2$ is selected from the group consisting of hydrogen, halogen, $NO_2$, CN, $C_1$ to $C_4$ alkyl or aryl, and $N(R^2)_2$ may form a 3 to 7 membered heterocyclic ring, for example pyrrolidine, 3-fluoropyrrolidine, piperidine, 4-fluoropiperidine, N-methylpiperazine, morpholine, 2,6-dimethylmorpholine, thiomorpholine; and said heterocyclic ring may be substituted with one or more of $R^2$; and $[C(R^2)_2]_c$ may form a 3 to 7 membered carbocyclic or heterocyclic ring;

$R^4$ and $R^5$ may be selected from the group consisting of hydrogen, halogen, $NO_2$, CN, $C_1$ to $C_8$ alkyl and aryl; or $CR^4R^5$ may form a 3 to 7 membered carbocyclic or heterocyclic ring;

A is 3 to 7 membered heterocyclic ring, e.g., A is a 5 or 6 membered heteroaryl radical represented by formula III below:

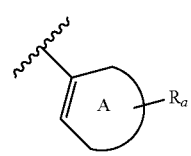

III wherein said heteroaryl radical is selected from the group consisting of:

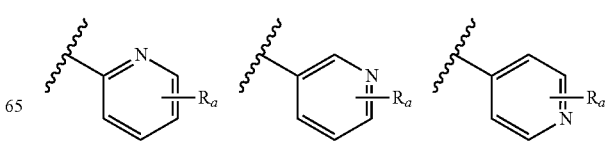

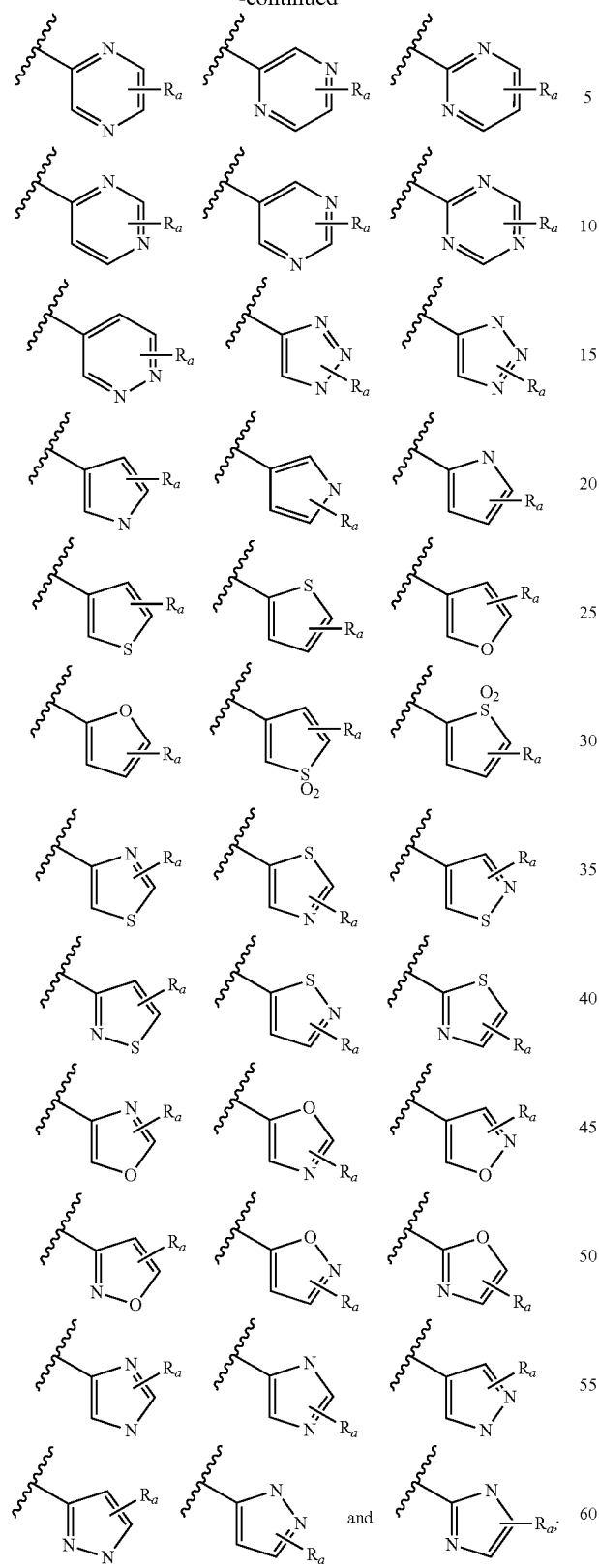

wherein R is selected from the group consisting of hydrogen, halogen, $C_1$ to $C_8$ alkyl, $CF_3$, $OCF_3$, $OCF_2H$, $CH_2CN$, $CN$, $SR^2$, $(CR^2R^8)_cC(O)OR^2$, $C(O)N(R^2)_2$, $(CR^7R^8)_cOR^2$, $HNC(O)R^2$, $HN-C(O)OR^2$, $C(O)NR^2(CR^2R^8)_cN(R^2)_2$, $NR^2C(O)(CR^7R^8)_cN(R^2)_2$, $(CR^7R^8)_cOC(O)(CR^7R^8)_cN(R^2)_2$, $(CR^7R^8)_cN(R^2)_2$, $SO_2(CR^7R^8)_cN(R^2)_2$, $OP(O)(OR^2)_2$, $OC(O)OR^2$, $OCH_2O$, $HN-CH=CH$, $-N(COR^2)CH_2CH_2$, $HC=N-NH$, $N=CH-S$, $O(CR^7R^8)_d-R^6$, $(CR^2R^8)_c-R^6$ and $(CR^2R^8)_cNR^2(CR^7R^8)_dR^6$; wherein R6 is selected from the group consisting of halogen, 3-fluoropyrrolidinyl, piperidinyl, 4-fluoropiperidinyl, N-methylpiperazinyl, 2,6-dimethylmorpholinyl, 3-fluoropiperidinyl, 2-pyridinyl, 3-pyridinyl, 4-pyridinyl, 3-pyrrolinyl, pyrrolidinyl, methyl isonipecotate, N-(2-methoxyethyl)-N-methylamyl, 1,2,3,6-tetrahydropyridinyl, morpholinyl, hexamethyleneiminyl, piperazinyl-2-one, piperazinyl, N-(2-methoxyethyl)ethylaminyl, thiomorpholinyl, heptamethyleneiminyl, 1-piperazinylcarboxaldehyde, 2,3,6,7-tetrahydro-(1H)-1,4-diazepinyl-5(4H)-one, N-methylhomopiperazinyl, (3-dimethylamino)pyrrolidinyl, N-(2-methoxyethyl)-N-propylaminyl, isoindolinyl, nipecotamidinyl, isonipecotamidinyl, 1-acetylpiperazinyl, 3-acetamidopyrrolidinyl, trans-decahydroisoquinolinyl, cis-decahydroisoquinolinyl, N-acetylhomopiperazinyl, 3-(diethylamino)pyrrolidinyl, 1,4-dioxa-8-azaspiro[4.5]decaninyl, 1-(2-methoxyethyl)-piperazinyl, 2-pyrrolidin-3-ylpyridinyl, 4-pyrrolidin-3-ylpyridinyl, 3-(methylsulfonyl)pyrrolidinyl, 3-picolylmethylaminyl, 2-(2-methylaminoethyl)pyridinyl, 1-(2-pyrimidyl)-piperazinyl, 1-(2-pyrazinyl)-piperazinyl, 2-methylaminomethyl-1,3-dioxolane, 2-(N-methyl-2-aminoethyl)-1,3-dioxolane, 3-(N-acetyl-N-methylamino)pyrrolidinyl, 2-methoxyethylaminyl, tetrahydrofurfurylaminyl, 4-aminotetrahydropyran, 2-amino-1-methoxybutane, 2-methoxyisopropylaminyl, 1-(3-aminopropyl)imidazole, histamyl, N,N-diisopropylethylenediaminyl, 1-benzyl-3-aminopyrrolidyl 2-(aminomethyl)-5-methylpyrazinyl, 2,2-dimethyl-1,3-dioxolane-4-methanaminyl, (R)-3-amino-1-N—BOC-pyrrolidinyl, 4-amino-1,2,2,6,6-pentamethylpiperidinyl, 4-aminomethyltetrahydropyran, ethanolamine and alkyl-substituted derivatives thereof; provided said alkyl or phenyl radicals may be substituted with one or two halo, hydroxy or lower alkyl amino radicals or said alkyl radicals may include enchained nitrogen or oxygen atoms, i.e. oxa or imino radicals, as, for example, in polyethylene(oxy)radicals and wherein $R^7$ and $R^8$ may be selected from the group consisting of H, hydroxyl, halogen, e.g. F, and C1 to C4 alkyl and CR7R8 may form a carbocyclic ring of from 3 to 6 carbons;

X' is selected from the group consisting of

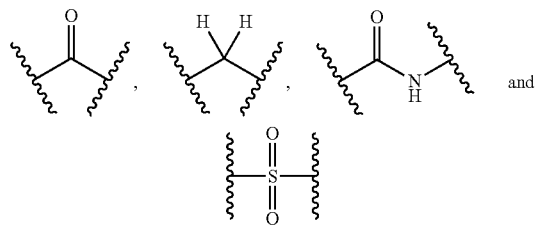

and B may be selected from the group consisting of hydrogen, hydroxy, $C_1$ to $C_8$ alkyl, aryl and $CR^4R^5$ wherein $CR^4R^5$ forms a 3 to 7 membered carbocyclic or heterocyclic ring, e.g., B may be a 5 or 6 membered aryl radical represented by formula III below:

III

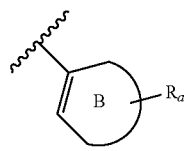

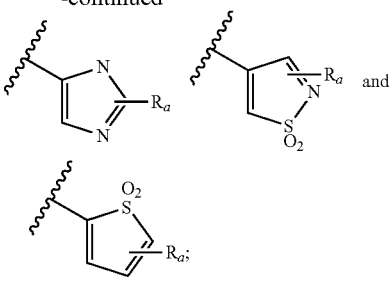

wherein said aryl is selected from the group consisting of:

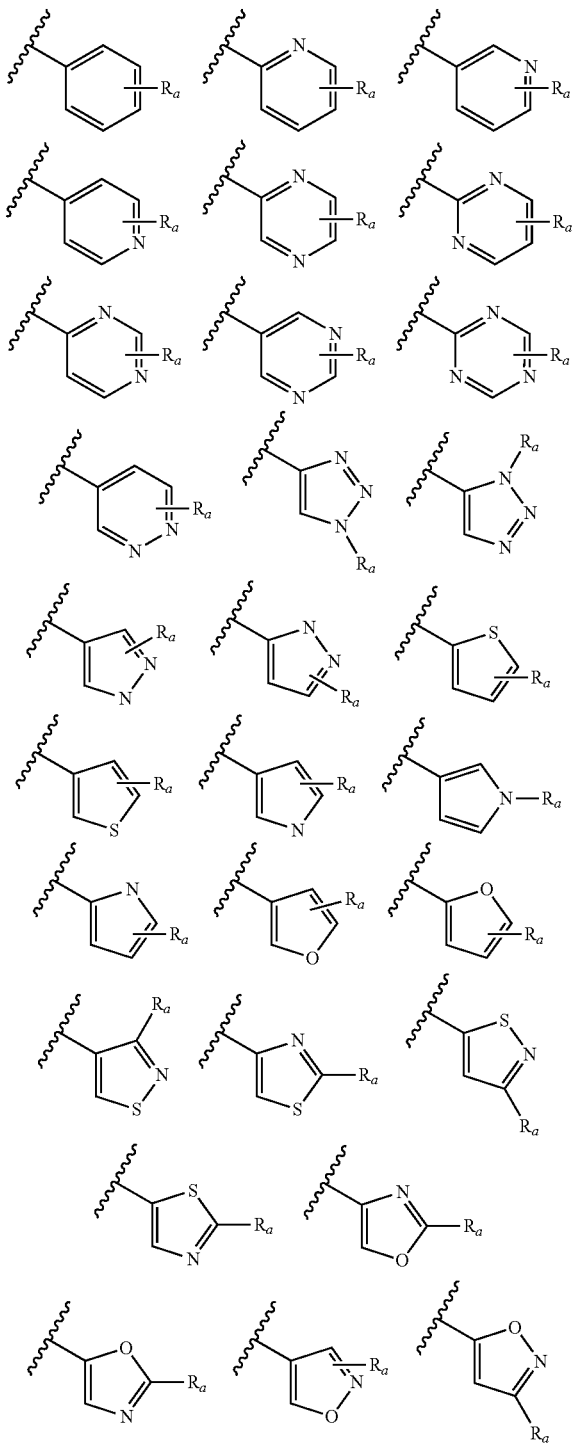

a is 0 or an integer of from 1 to 5, preferably 1 to 3;
c is 0 or an integer of from 1 to 4;
d is an integer of from 2 to 5;
the wavy line represents an E or Z bond and pharmaceutically acceptable salts thereof.
Preferably Z, $R^1$ and $R^3$ are H.
Preferably X' is selected from the group consisting of

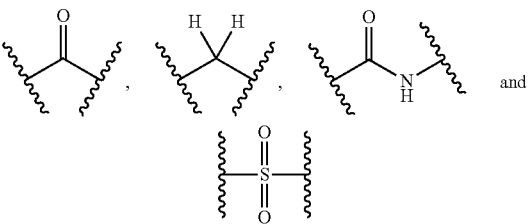

Preferably B is selected from the group consisting of 5-membered heterocyclic aryl radicals and 6-membered carbocyclic aryl radicals.
More preferably, X is

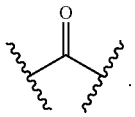

More preferably, X' is

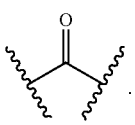

More preferably, B is a 5-membered heterocyclic aryl radical wherein the heterocyclic ring comprises one oxygen or sulfur atom or two nitrogen atoms.
More preferably, said heterocyclic aryl radical is substituted with a lower alkyl group or a halogen radical.

In another embodiment, B is phenyl and said phenyl radical may be substituted with a lower alkyl radical.

Preferably a is 1 or 2 and at least one R is H or OH or a is 1 and R is selected from the group consisting of carboxylic acid radicals, and 5 or 6 membered heterocyclic radicals wherein the heterocyclic ring includes a first enchained nitrogen atom and optionally, an enchained oxygen atom or a second enchained nitrogen atom.

Preferably R includes a carboxylic acid radical which is covalently bonded to a phenyl group through a polymethylene group, e.g. an ethylenyl or a propylenyl group.

Preferably R includes a heterocyclic ring which is directly bonded to the phenyl group or indirectly through a polymethylene group wherein, in either case, said bond is through an enchained nitrogen atom in said heterocyclic ring.

More preferably, said heterocyclic ring is selected from the group consisting of pyrrolidine, morpholine, piperazine and piperidine and said heterocyclic ring is substituted with a lower alkyl or a hydroxyl radical.

R may be

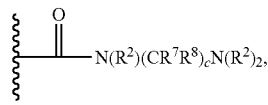

R is

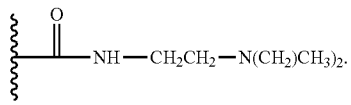

In another embodiment, B is selected from the group consisting of furyl, thienyl, pyrazole and imidazole.

The following abbreviations may be used throughout this specification.

"Ac" refers to acetyl.
"Ar" refers to aryl.
"Tf" refers to triflate.
"Me" refers to methyl.
"Et" refers to ethyl.
"tBu" refers to t-butyl.
"iPr" refers to I-propyl.
"Ph" refers to phenyl.

"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"Alkyl" refers to a straight-chain, branched or cyclic saturated aliphatic hydrocarbon.

Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino, and SH.

"Alkenyl" refers to a straight-chain, branched or cyclic unsaturated hydrocarbon group containing at least one carbon-carbon double bond. Preferably, the alkenyl group has 1 to 12 carbons. More preferably it is a lower alkenyl of from 1 to 7 carbons, most preferably 1 to 4 carbons. The alkenyl group may be optionally substituted with one or more substituents selected from the group consisting of hydroxyl, cyano, alkoxy, =O, =S, $NO_2$, halogen, dimethyl amino, and SH.

"Alkynyl" refers to a straight-chain, branched or cyclic unsaturated hydrocarbon containing at least one carbon-carbon triple bond. Preferably, the alkynyl group has 1 to 12 carbons. More preferably it is a lower alkynyl of from 1 to 7 carbons, most preferably 1 to 4 carbons. The alkynyl group may be optionally substituted with one or more substituents selected from the group consisting of hydroxyl, cyano, alkoxy, =O, =S, $NO_2$, halogen, dimethyl amino, and SH.

"Alkoxyl" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino "Alkaryl" refers to an alkyl that is covalently joined to an aryl group. Preferably, the alkyl is a lower alkyl.

"Carbocyclic aryl" refers to an aryl group wherein the ring atoms are carbon.

"Heterocyclic aryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Amide" refers to —C(O)—NH—R', wherein R' is alkyl, aryl, alkylaryl or hydrogen.

"Thioamide" refers to —C(S)—NH—R', wherein R' is alkyl, aryl, alkylaryl or hydrogen.

"Amine" refers to a —N(R")R''' group, wherein R" and R''' are independently selected from the group consisting of alkyl, aryl, and alkylaryl.

"Thioether" refers to —S—R", wherein R" is alkyl, aryl, or alkylaryl.

"Sulfonyl" refers to —S(O)$_2$—R'''', where R'''' is aryl, C(CN)=C-aryl, $CH_2CN$, alkylaryl, sulfonamide, NH-alkyl, NH-alkylaryl, or NH-aryl.

Illustrative routes to compounds of the present invention are illustrated in Schemes I, II, III, IV and V set forth below and are not intended to limit the scope of the invention.

Scheme I: Preparation of IIIa & IIIB (5-(3, and 4-Amino-benzoyl)-1,3-dihydro-indol-2-one) and IVa & IVb (5-(3, and 4-Amino-benzoyl)-1,3-dihydro-indol-2-one).
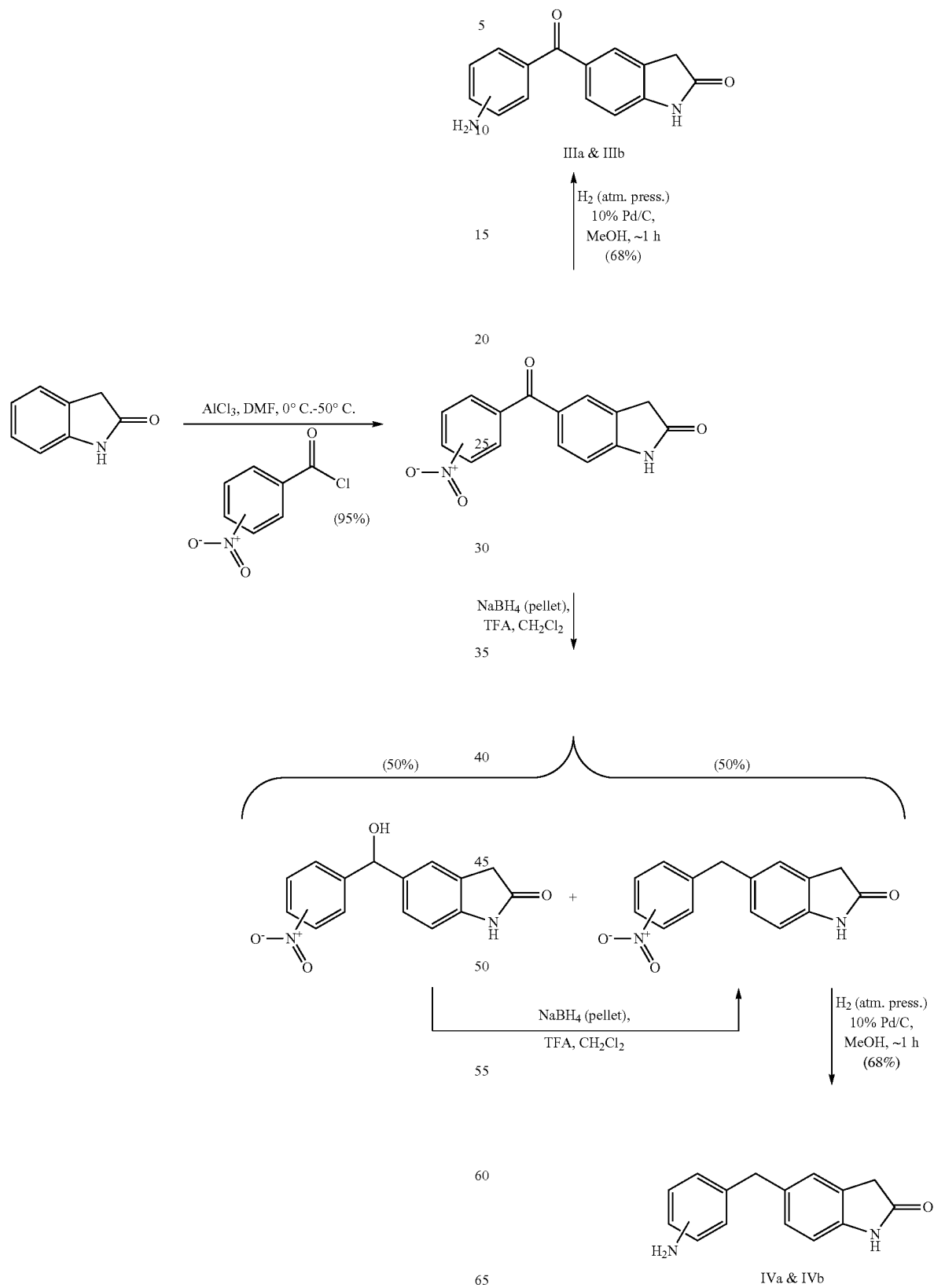

Wherein IVa & IVb are specific embodiments of Formula II in which X=CH$_2$;
Scheme II: Preparation of Ia: 6-(4-Amino-benzoyl)-1,3-dihydro-indol-2-one.
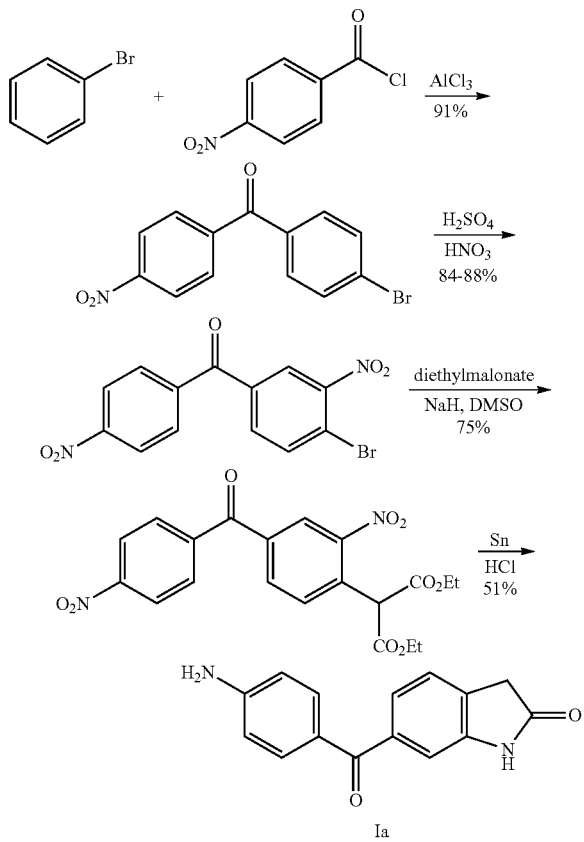
Ia
Scheme III: Preparation of Ib: 6-(3-Amino-benzoyl)-1,3-dihydro-indol-2-one.
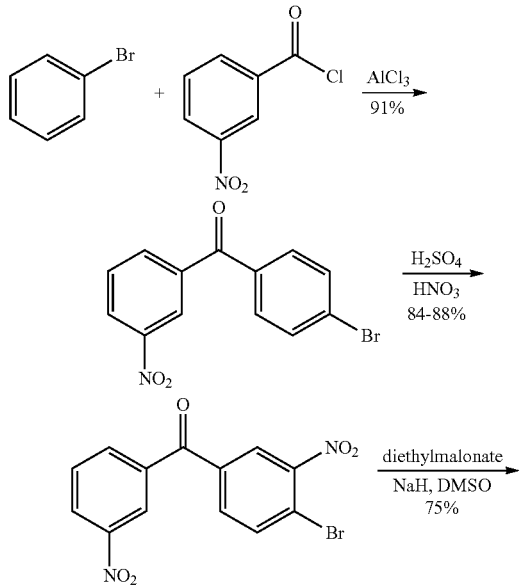
-continued
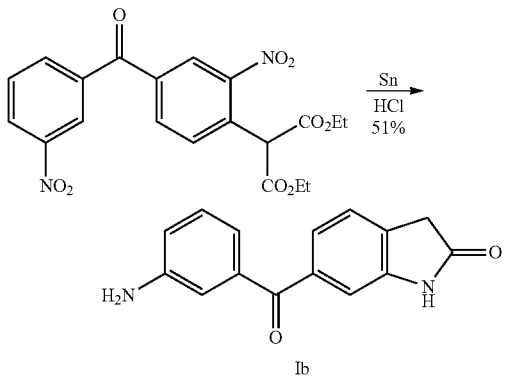
Ib
Wherein Ia of Scheme II and Ib of Scheme III are specific embodiments of Formula I in which
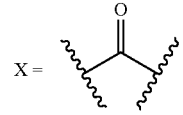
Scheme IV:
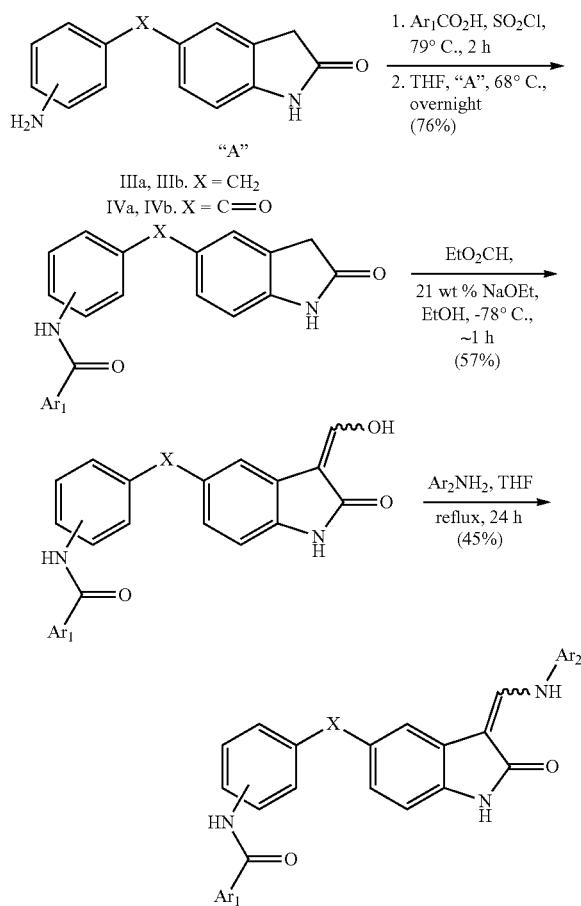

Wherein X in Scheme IV represents X in Formula II, Ar$_2$ of Scheme IV represents A in Formula II, and COAr$_1$ of Scheme IV represents X'B in Formula II.

Scheme V:

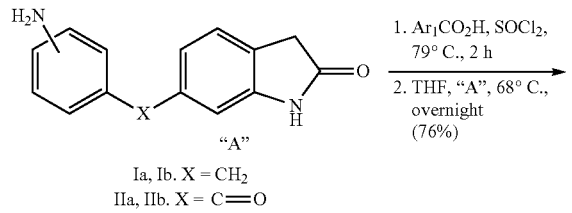

Ia, Ib. X = CH$_2$
IIa, IIb. X = C=O

1. Ar$_1$CO$_2$H, SOCl$_2$, 79° C., 2 h
2. THF, "A", 68° C., overnight (76%)

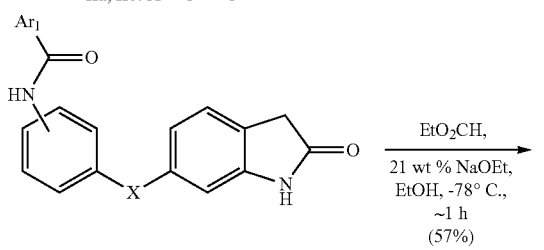

EtO$_2$CH, 21 wt % NaOEt, EtOH, −78° C., ~1 h (57%)

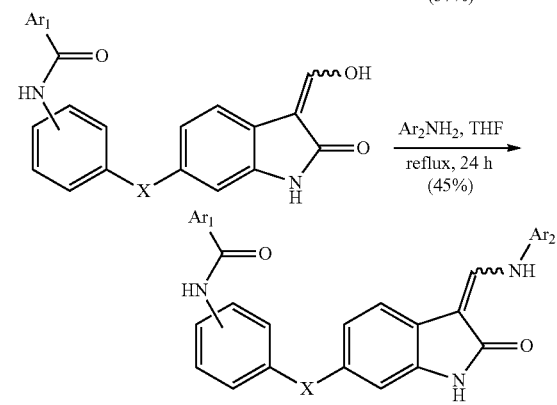

Ar$_2$NH$_2$, THF reflux, 24 h (45%)

Wherein X of Scheme V represents X in Formula I, and COAr$_1$ of Scheme V represents X'B of Formula I.

Specific Compounds of the invention include:
Molstructure

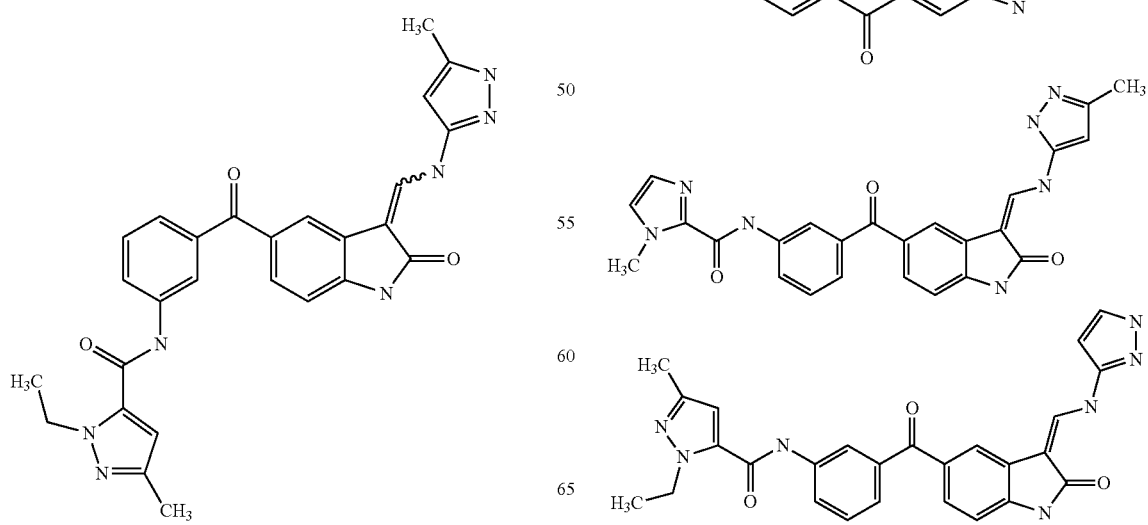

17
-continued
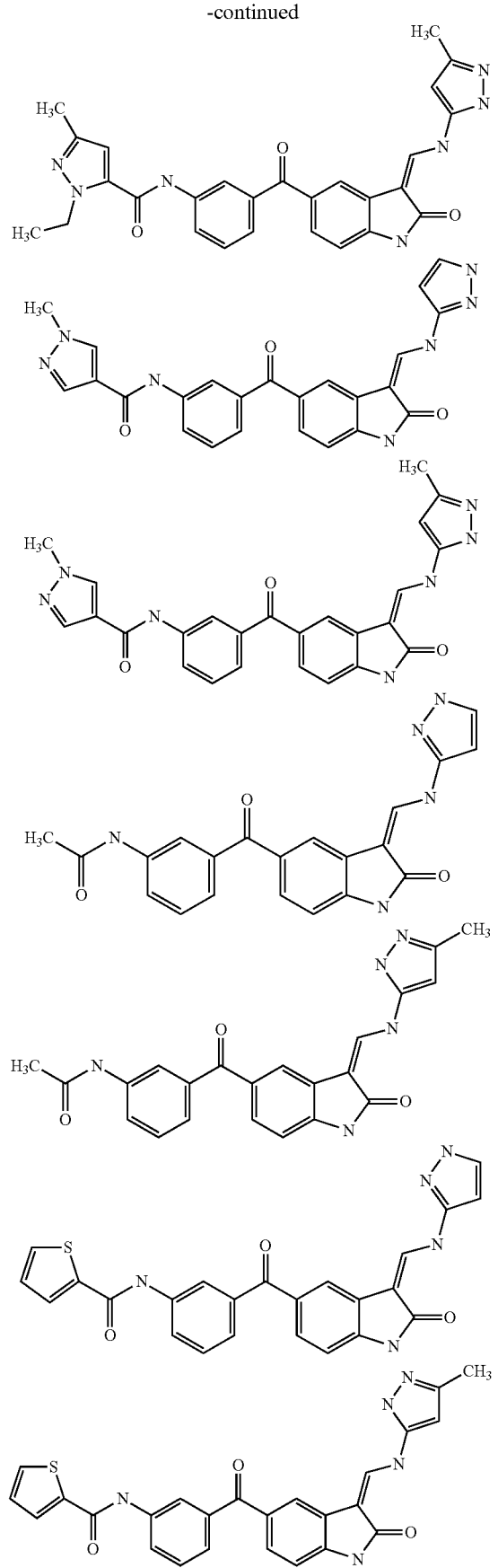
18
-continued
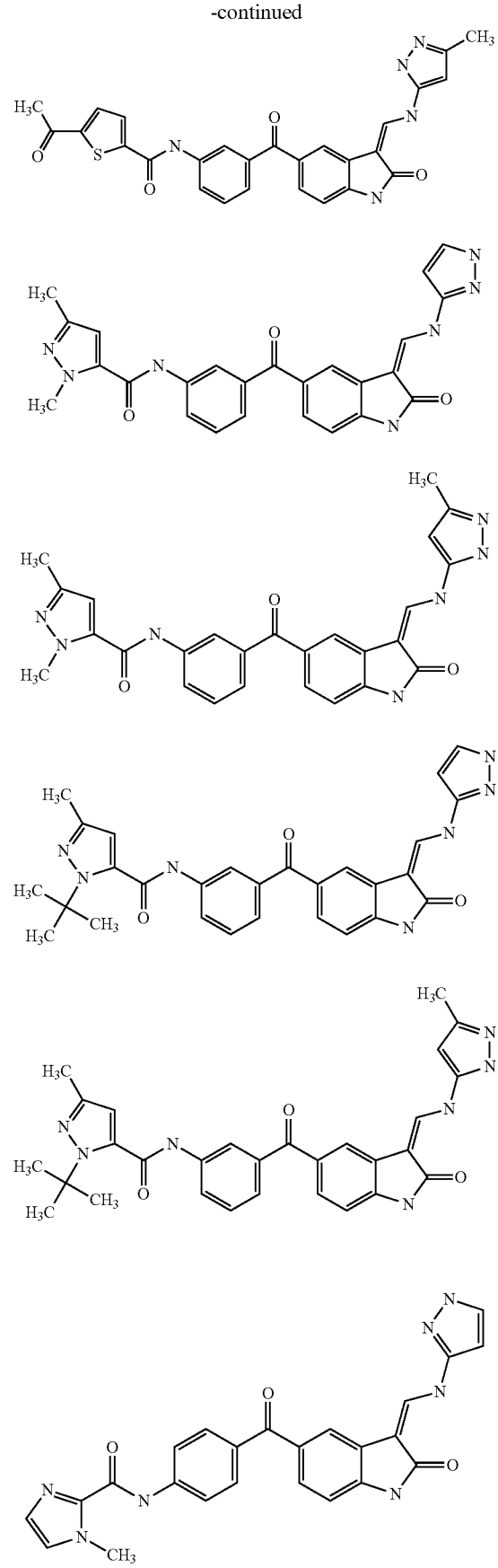

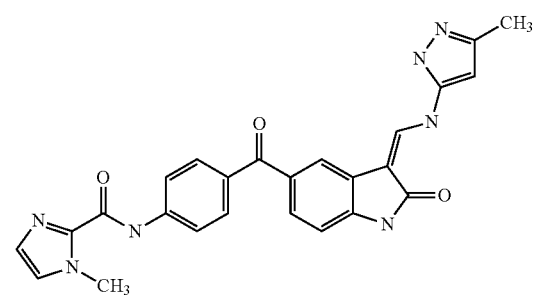
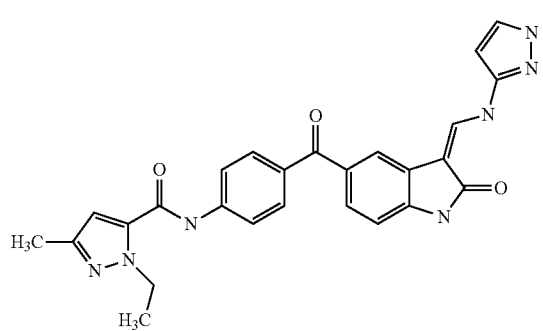
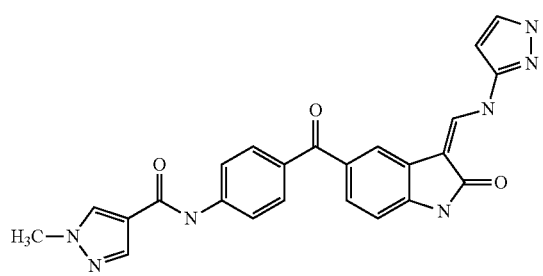
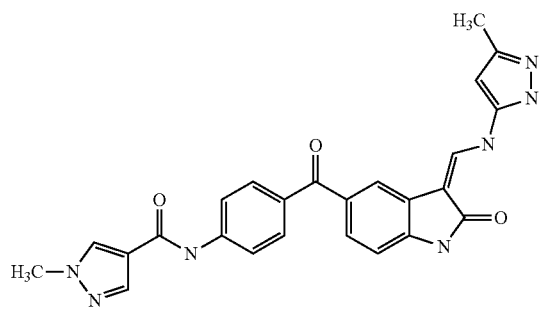
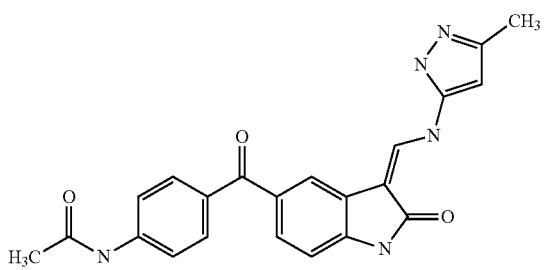
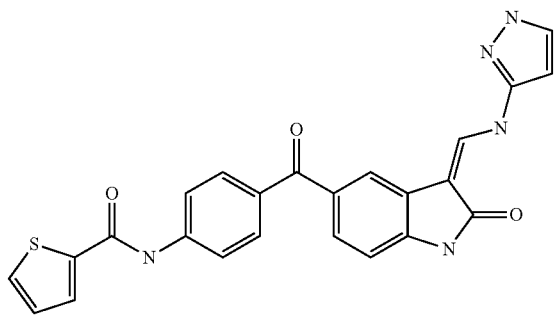
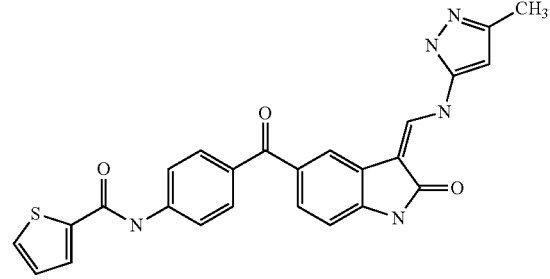
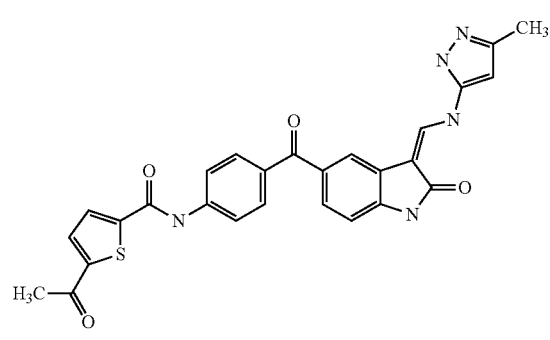
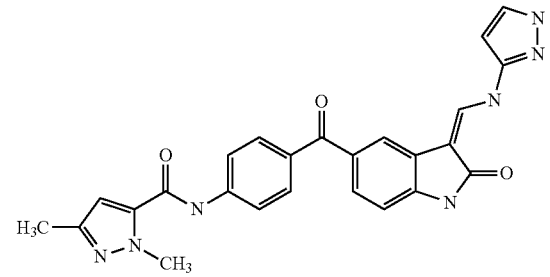
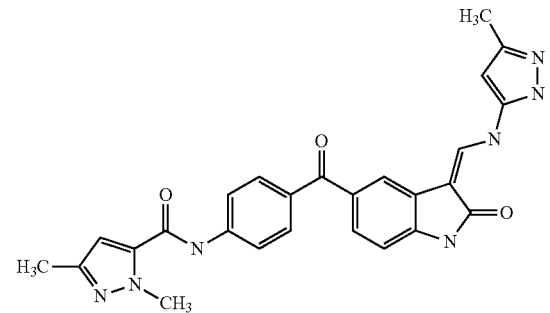

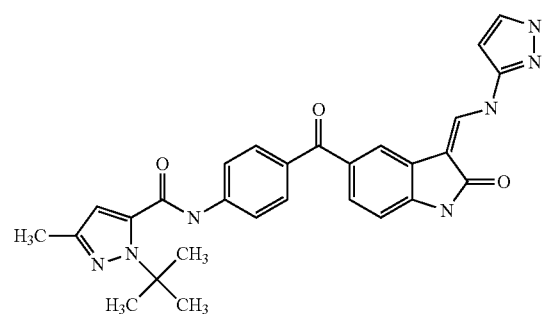
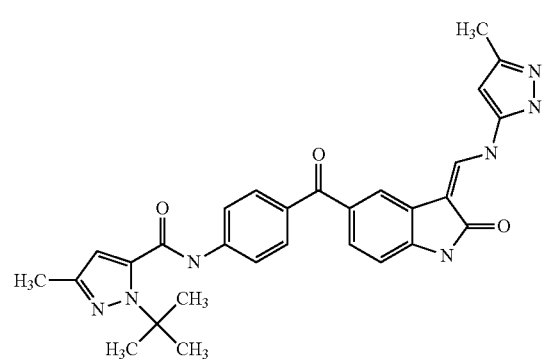
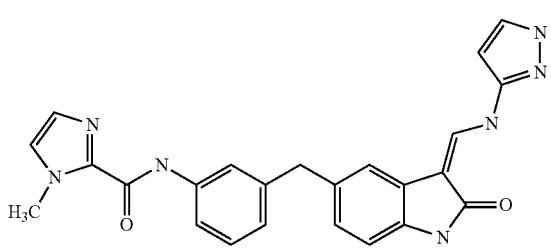
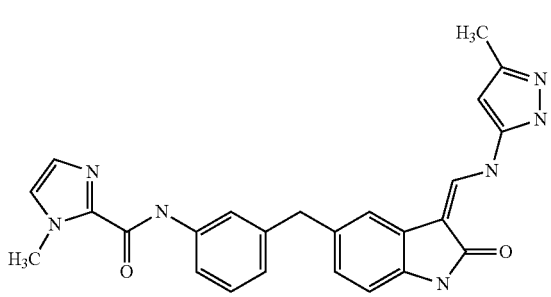
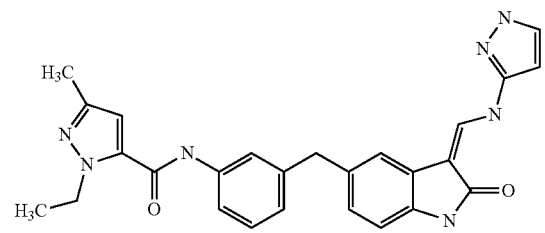
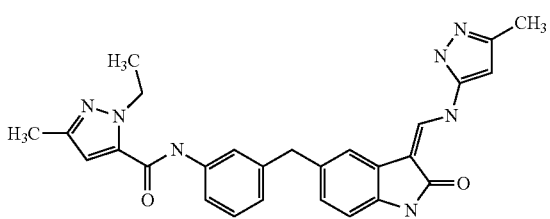
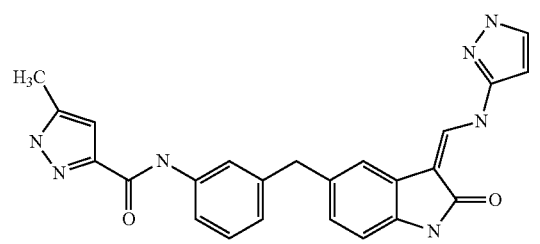
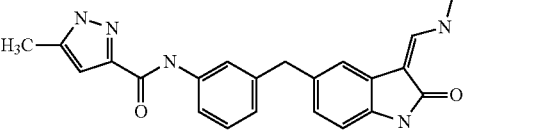
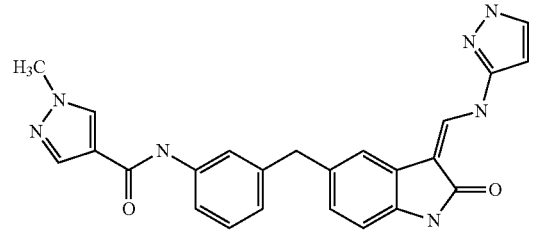
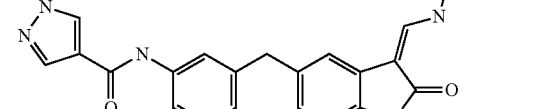
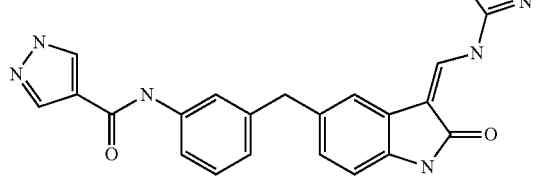
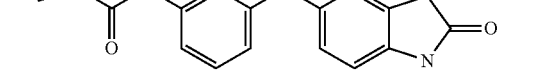
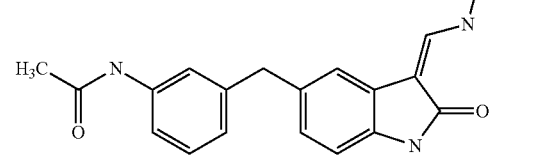

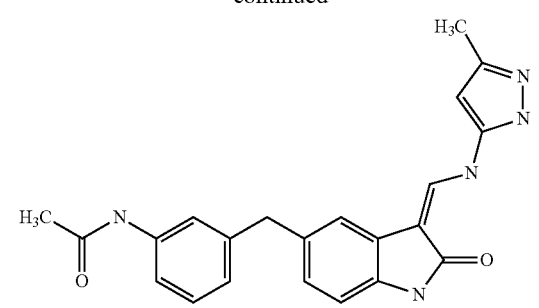
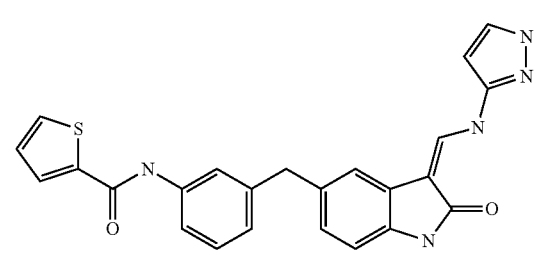
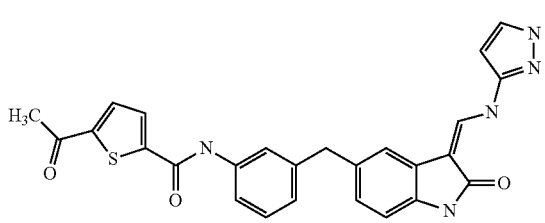
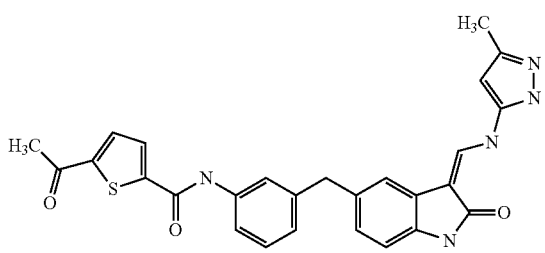
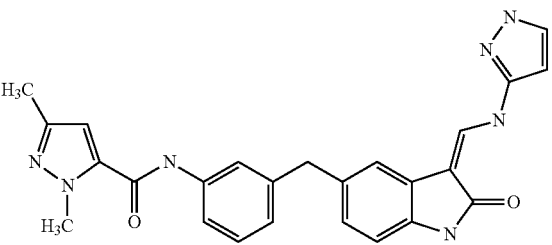
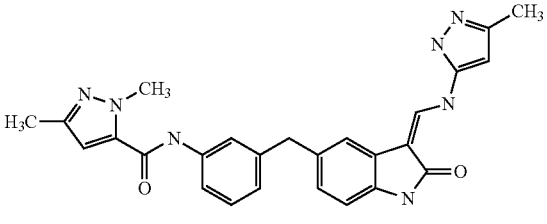
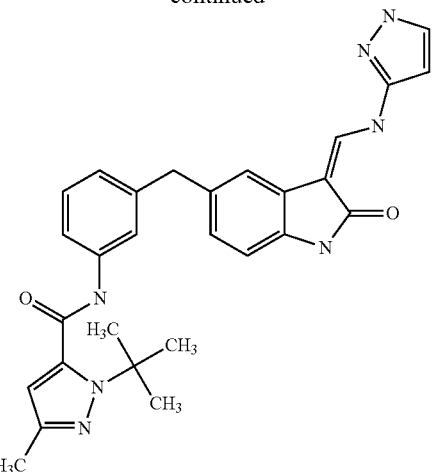
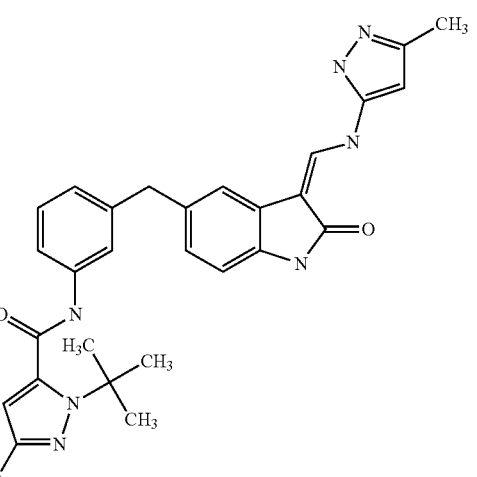
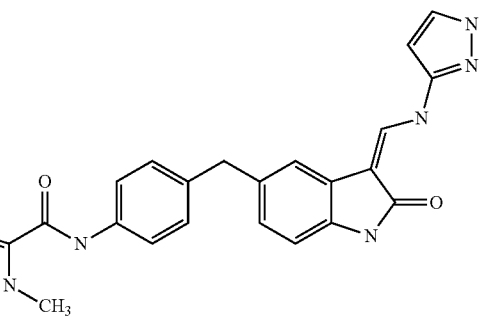
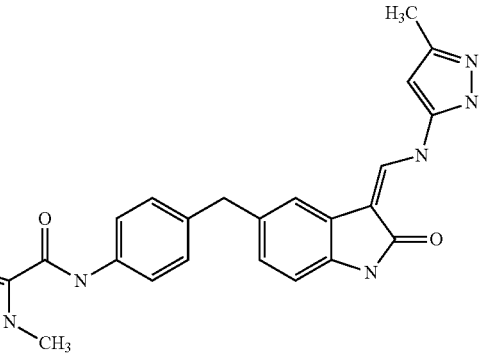

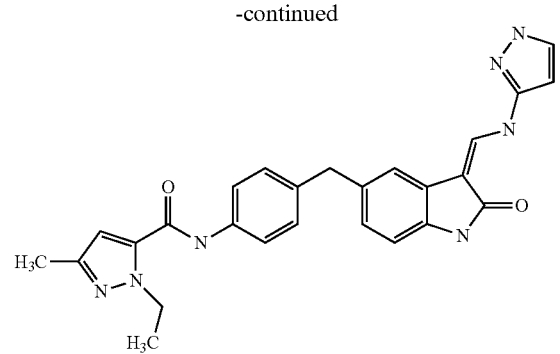
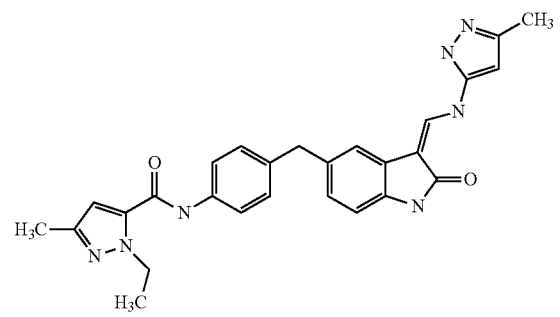
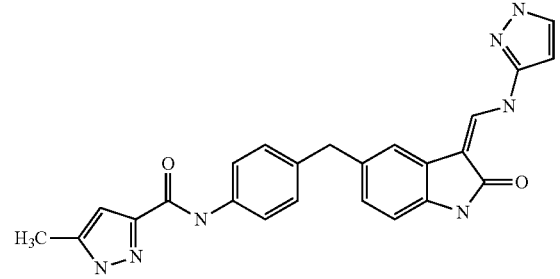
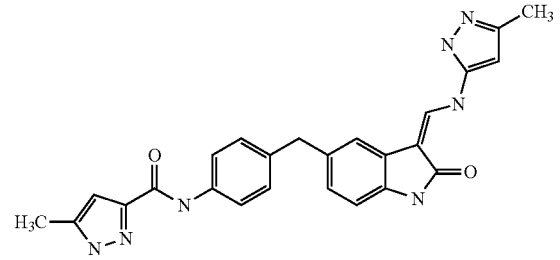
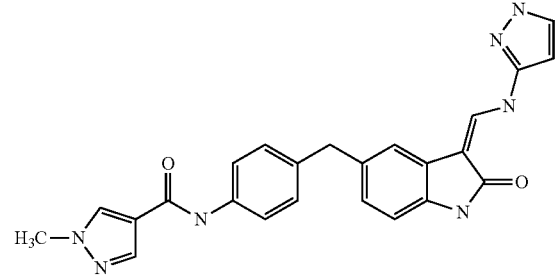
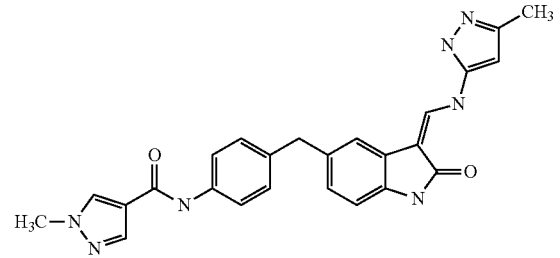
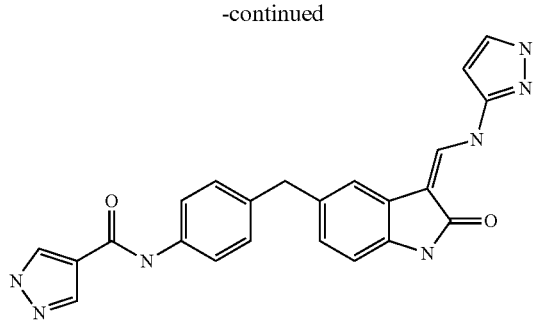
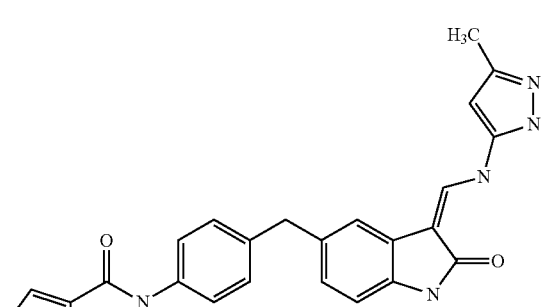
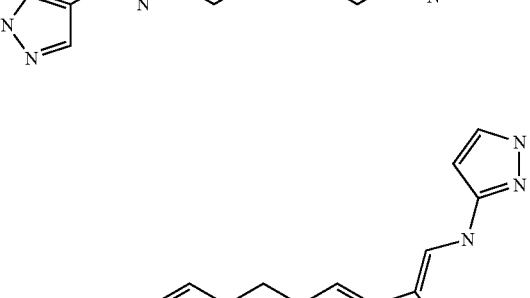
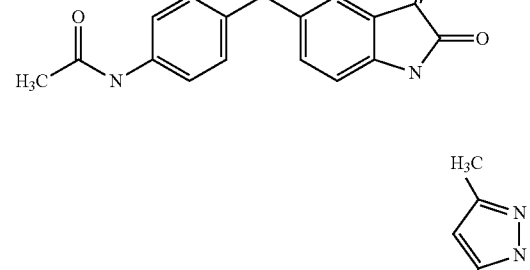
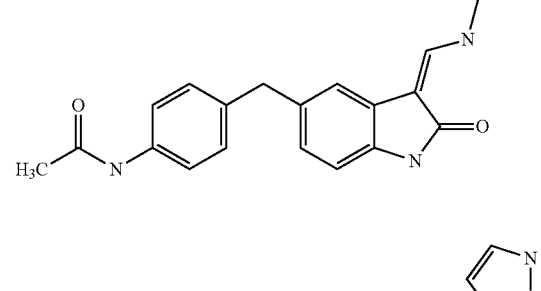
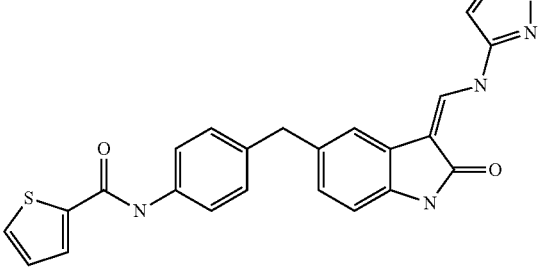

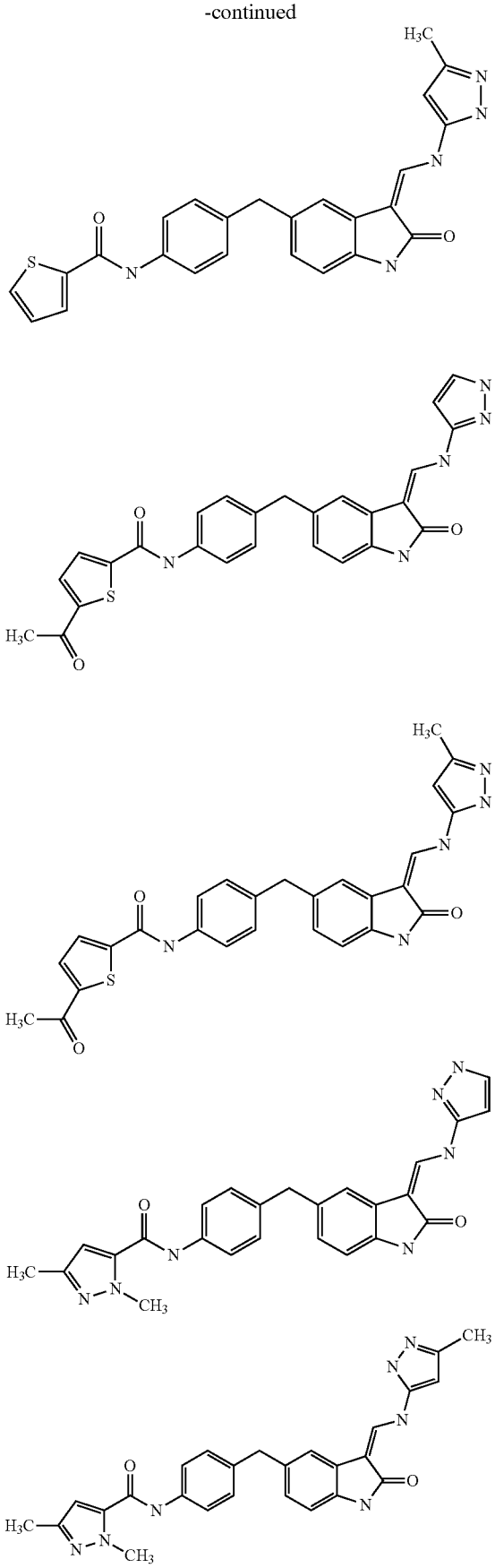

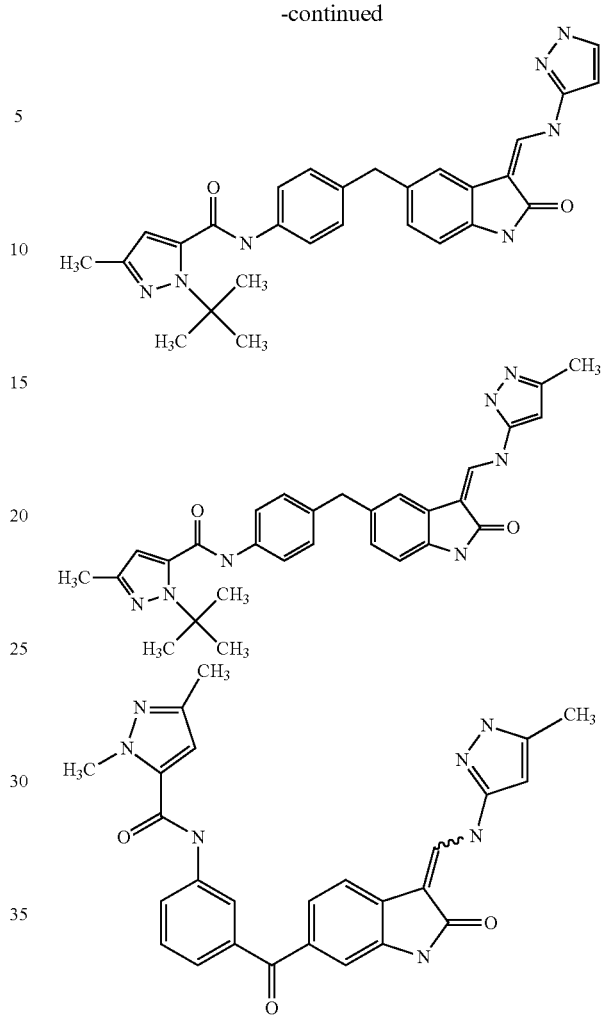

The present invention is further directed to pharmaceutical compositions comprising a pharmaceutically effective amount of the above-described compounds and a pharmaceutically acceptable carrier or excipient. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, atherosclerosis, arthritis, and other disorders related to abnormal vasculogenesis and/or angiogenesis, such as diabetic retinopathy.

The present invention relates to compounds capable of regulating and/or modulating tyrosine kinase signal transduction and more particularly receptor and non-receptor tyrosine kinase signal transduction.

Receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects and responses to the extracellular microenvironment).

It has been shown that tyrosine phosphorylation sites in growth factor receptors function as high-affinity binding sites for SH2 (src homology) domains of signaling molecules. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Tyrosine kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis, e.g. macular degeneration).

This invention is therefore directed to compounds which regulate, modulate and/or inhibit tyrosine kinase signal transduction by affecting the enzymatic activity of the RTKs and/or the non-receptor tyrosine kinases and interfering with the signal transduced by such proteins. More particularly, the present invention is directed to compounds which regulate, modulate and/or inhibit the RTK and/or non-receptor tyrosine kinase mediated signal transduction pathways as a therapeutic approach to cure many kinds of solid tumors, including but not limited to carcinoma, sarcoma, leukemia, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers.

All references cited herein are hereby incorporated by reference in their entirety.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof.

The invention claimed is:

1. A compound selected from the group consisting of:

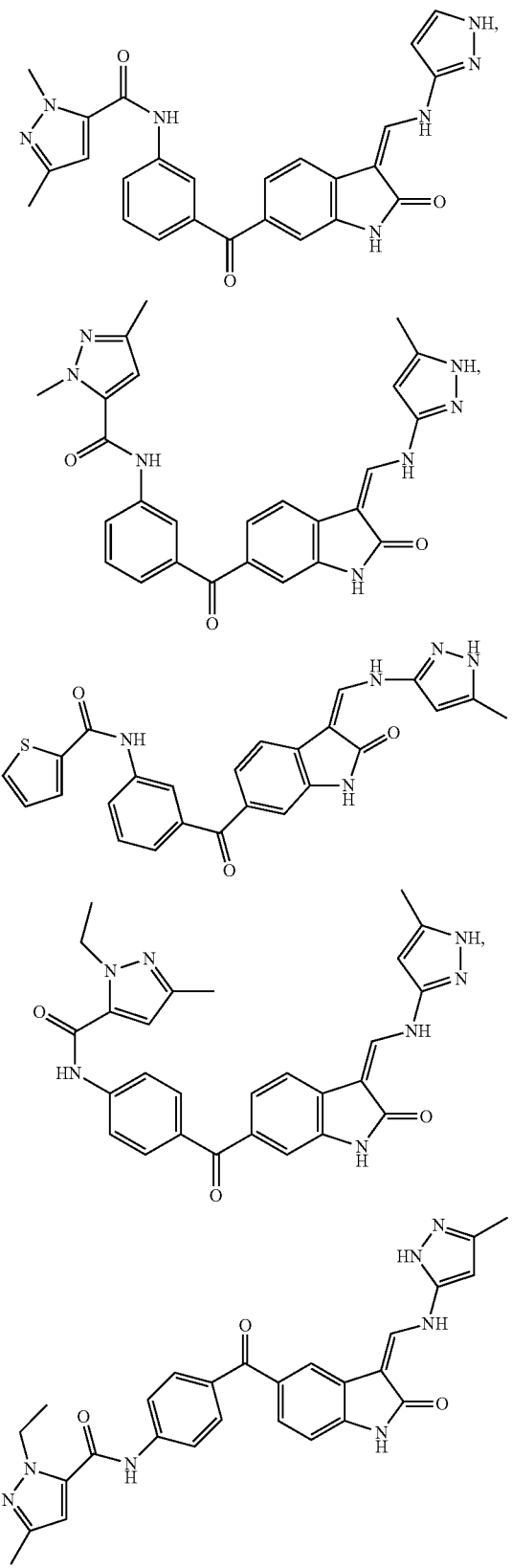

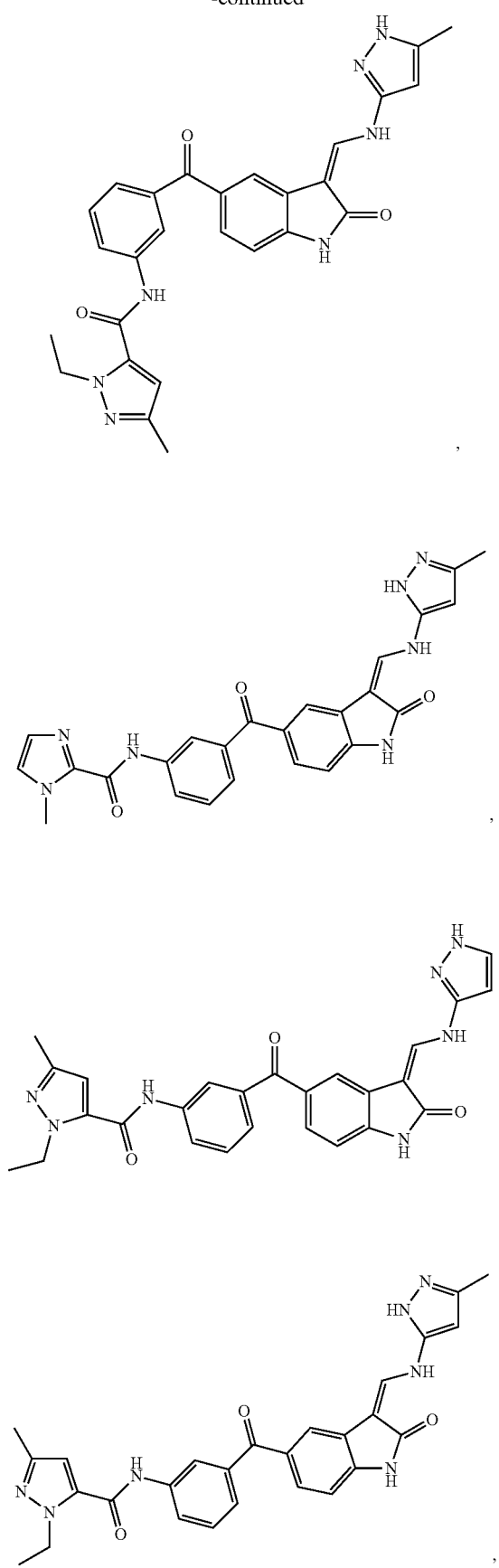
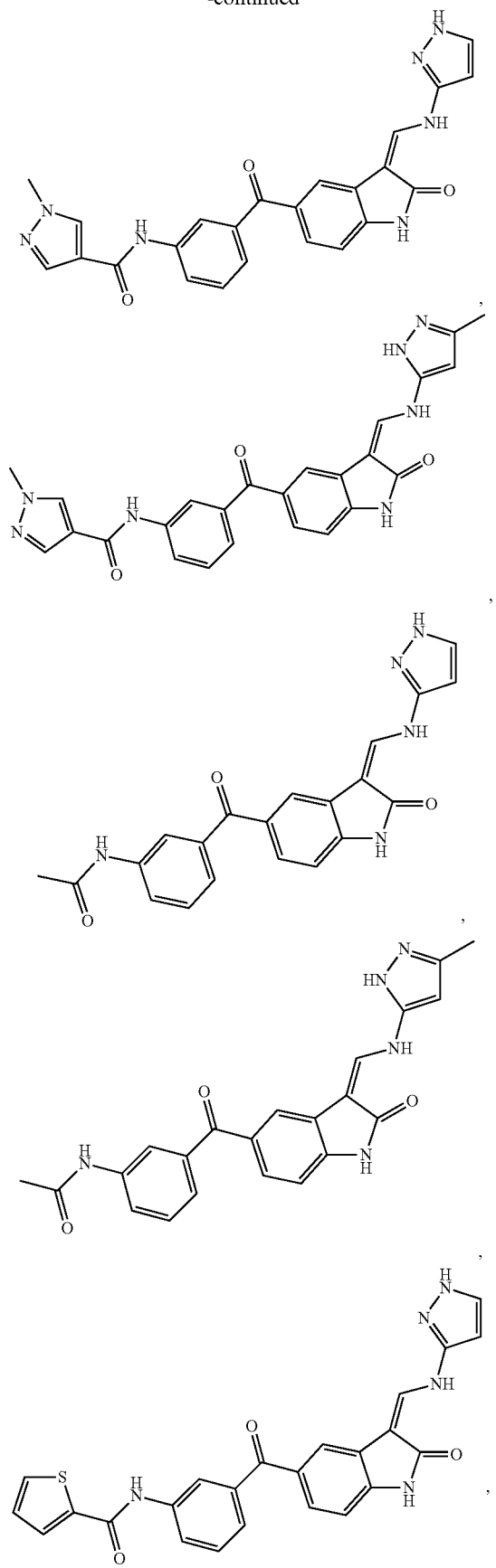

33
-continued
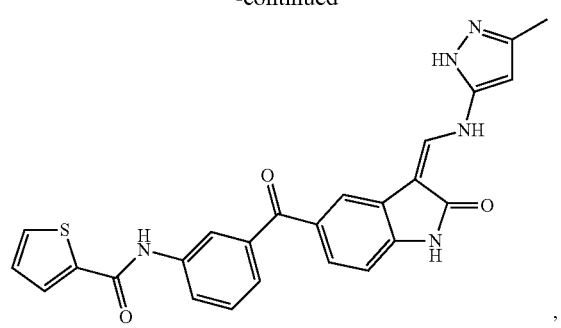
,
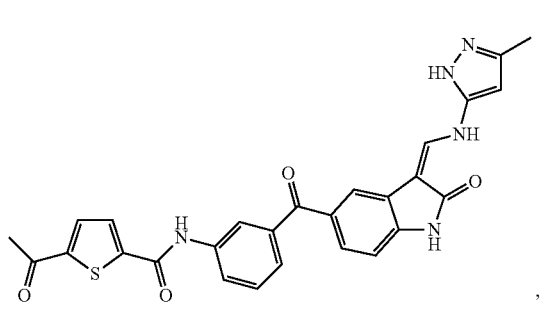
,
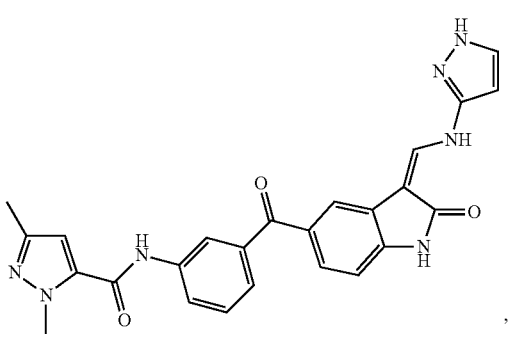
,
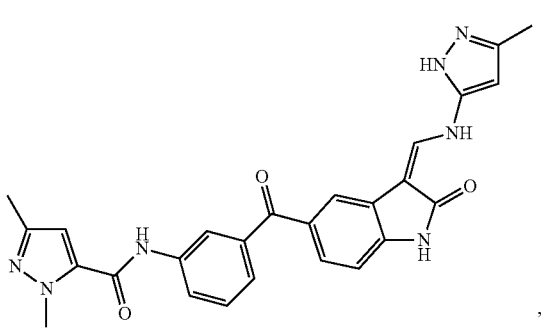
,
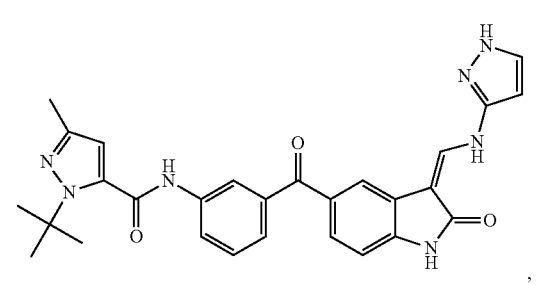
,
34
-continued
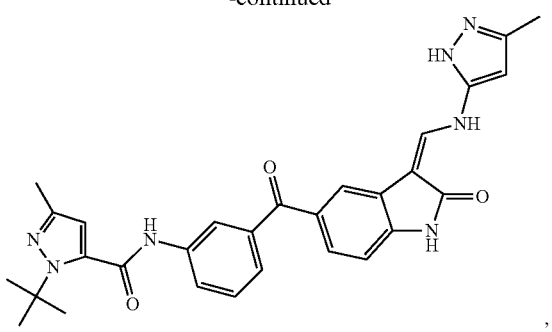
,
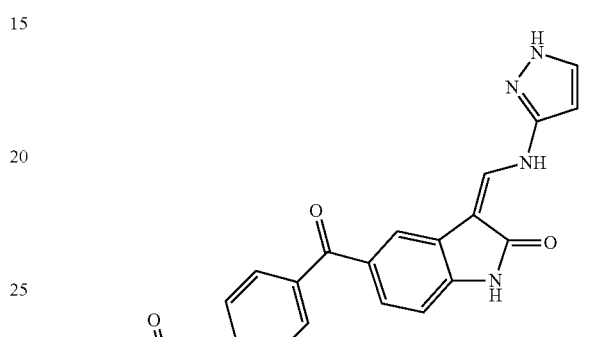
,
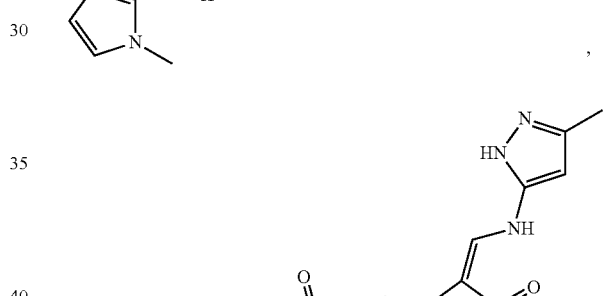
,
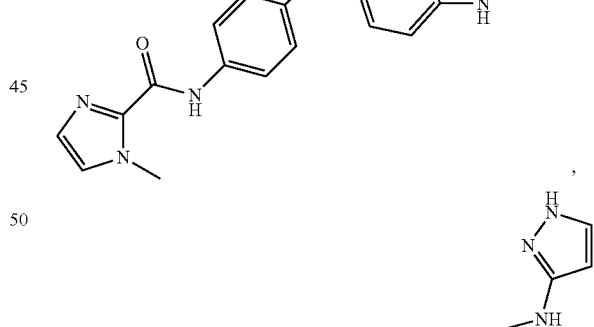
,
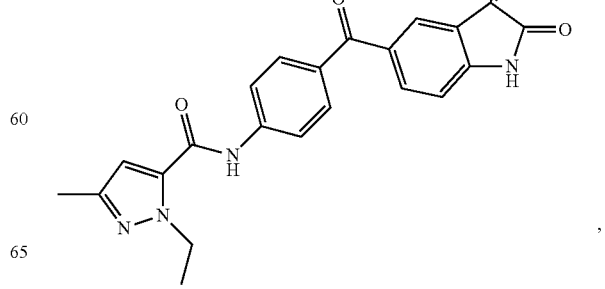
, -continued
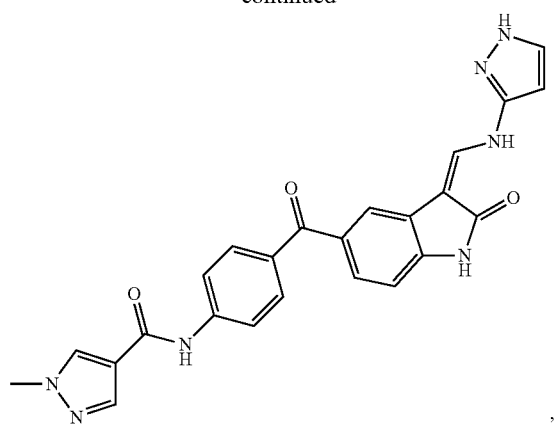
,
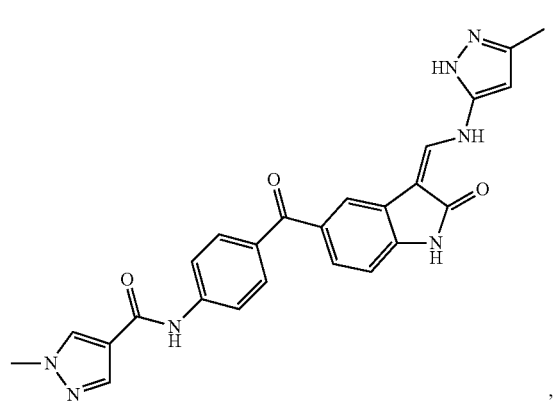
,
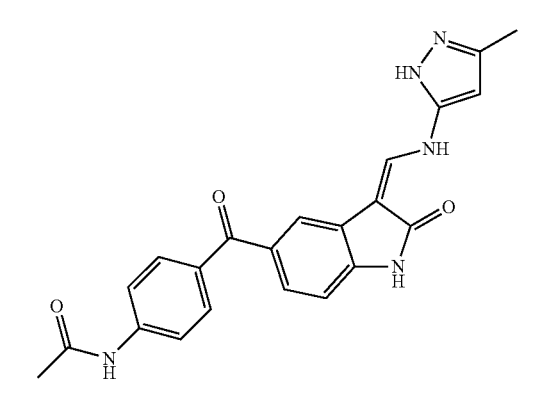
,
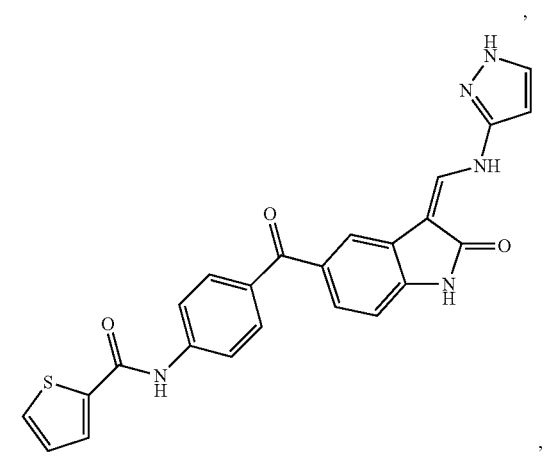
,
-continued
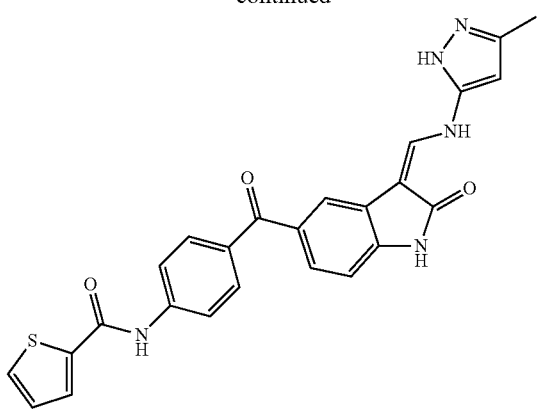
,
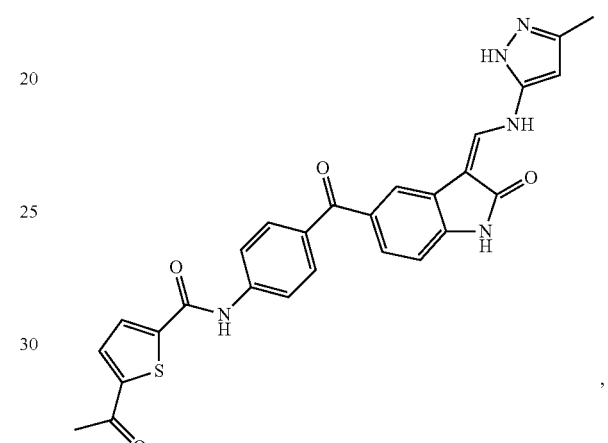
,
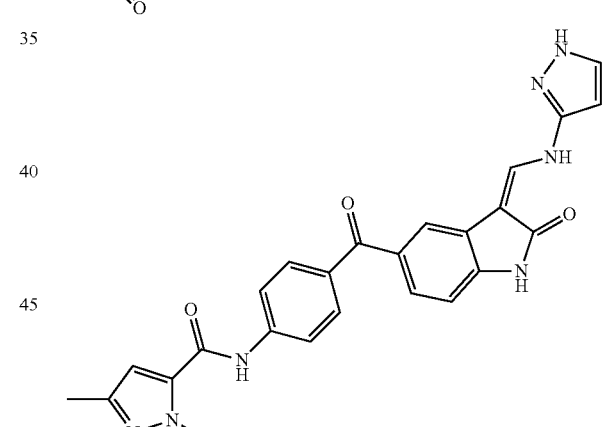
,
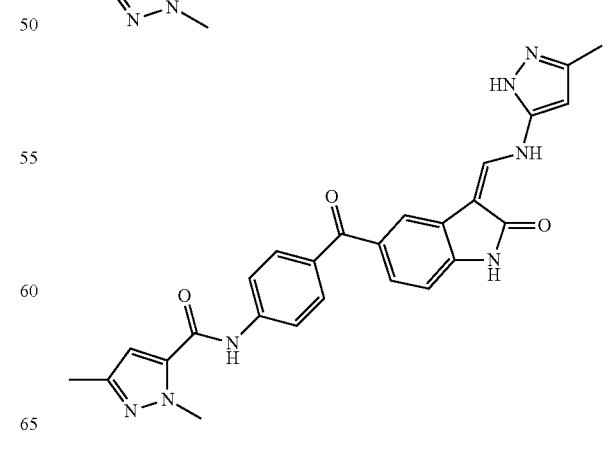
,

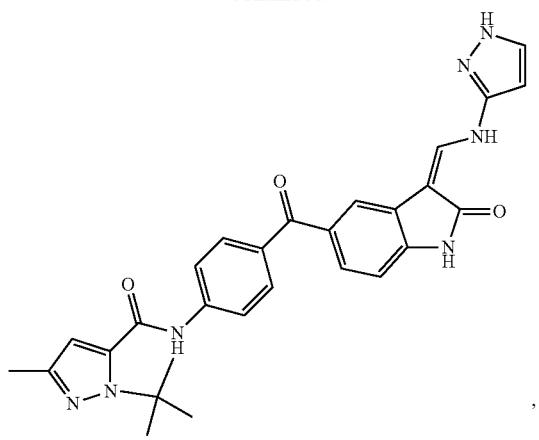
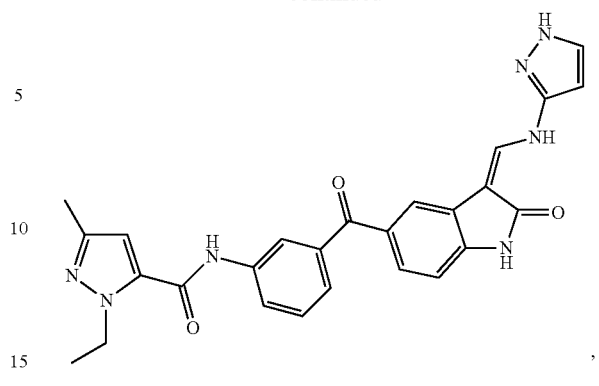
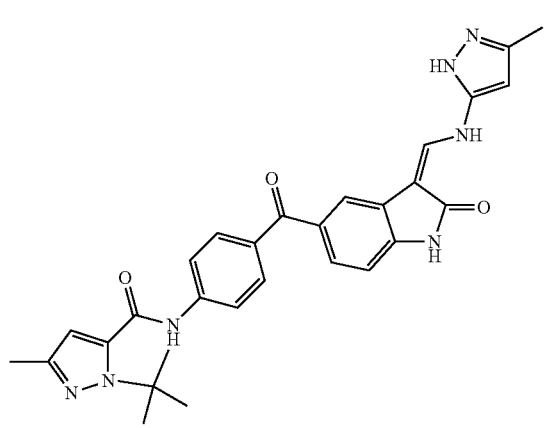
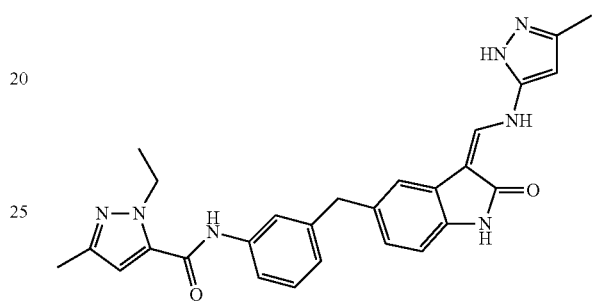
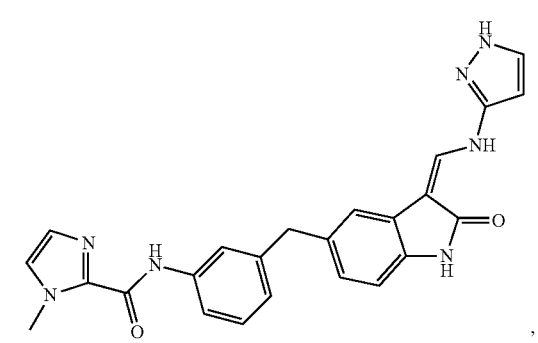
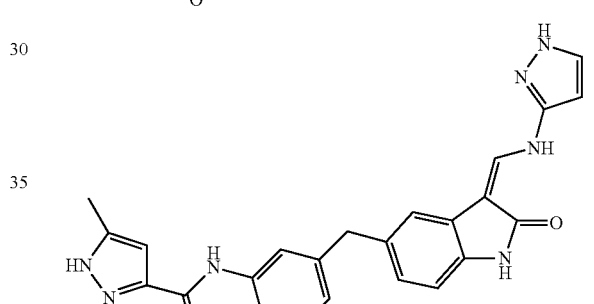
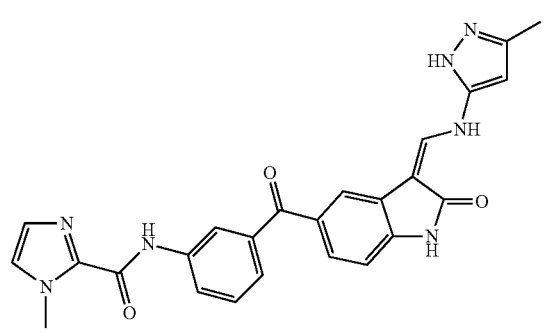
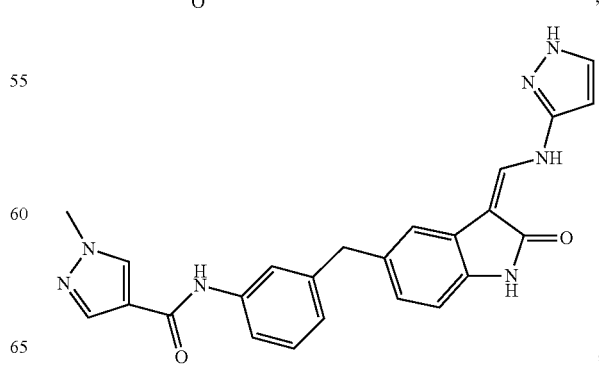

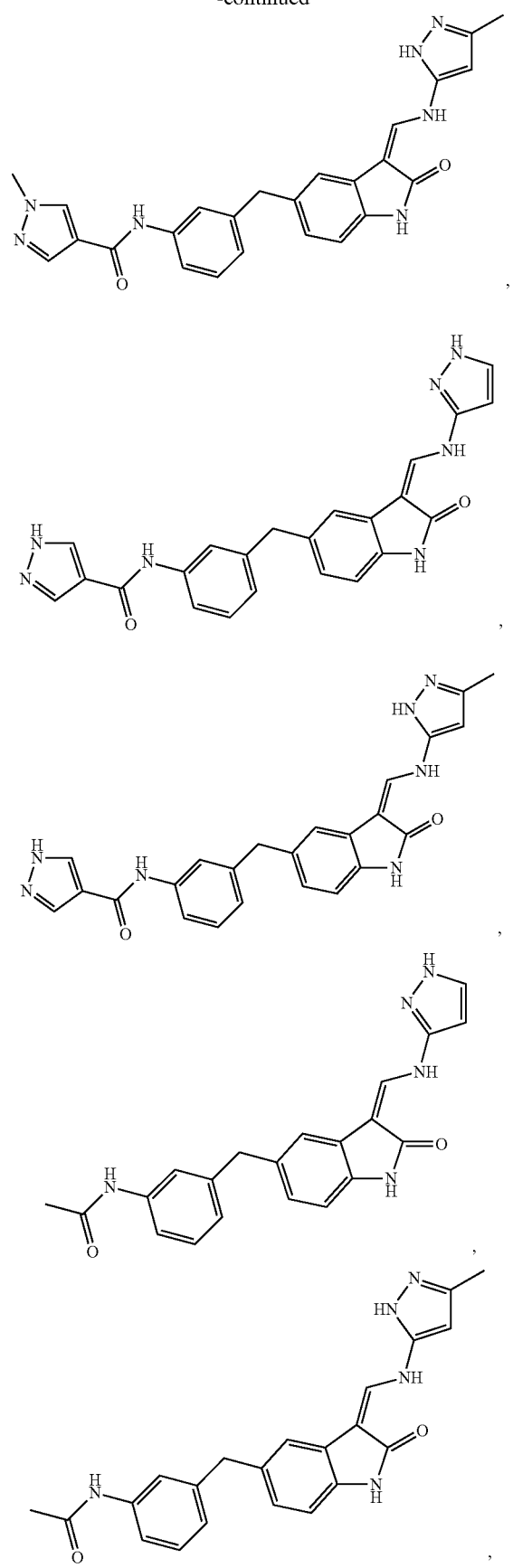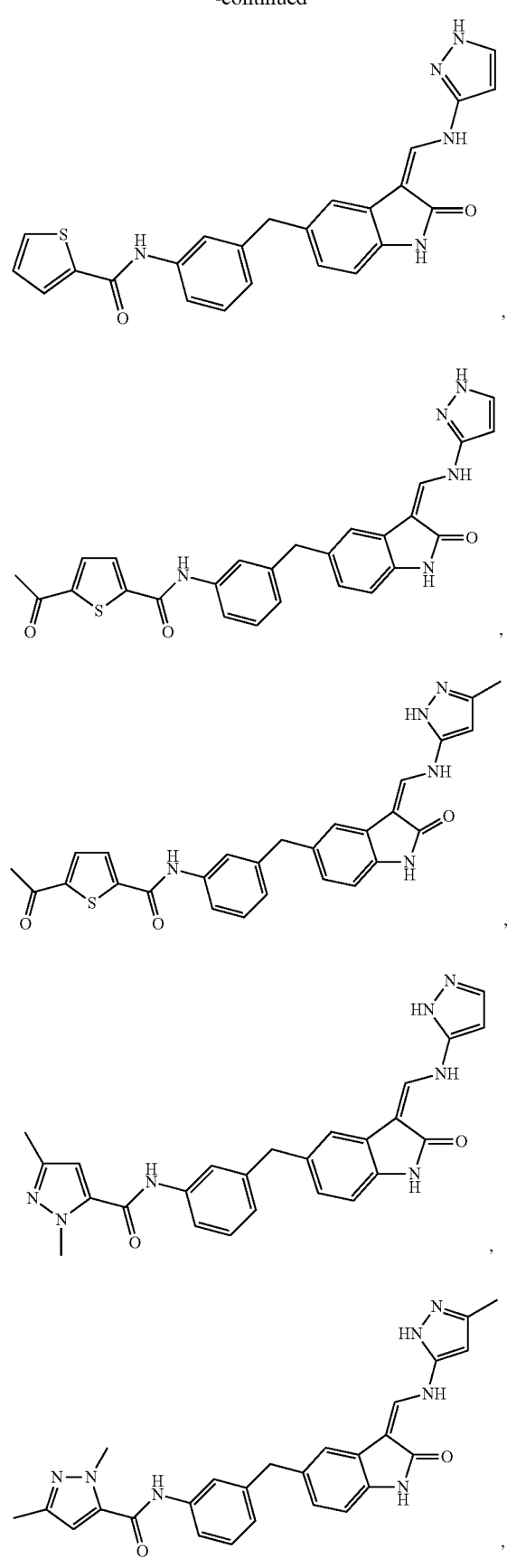

41
-continued
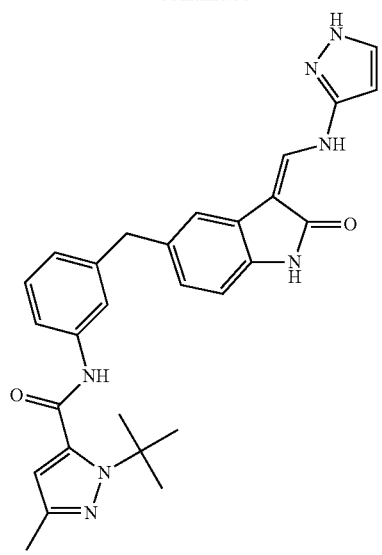
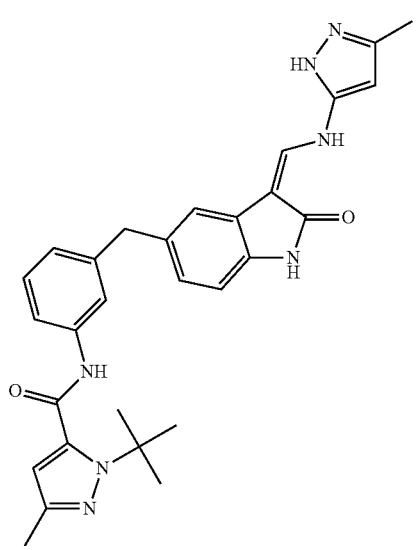
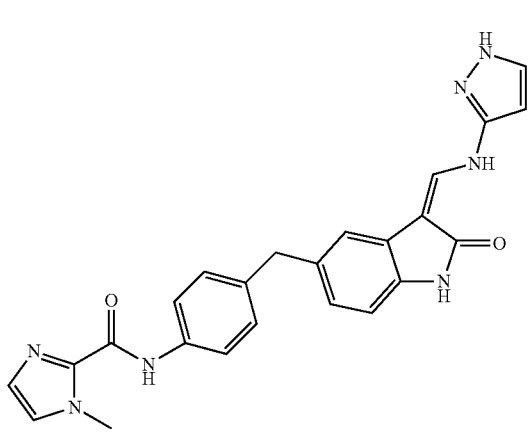
42
-continued
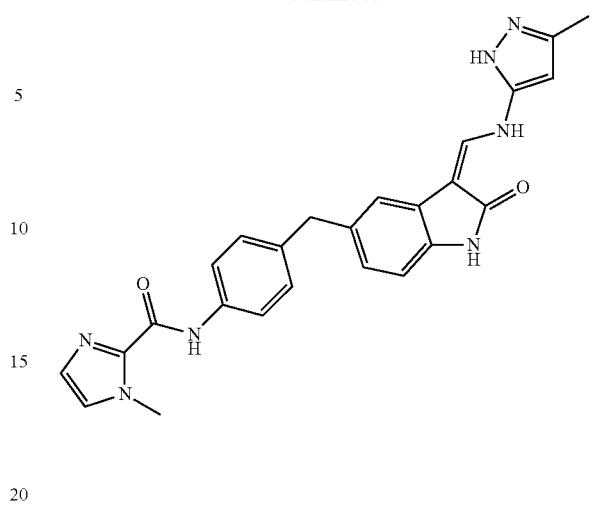
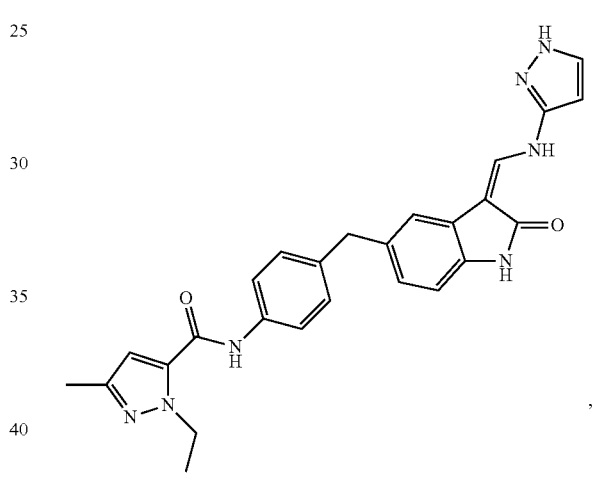
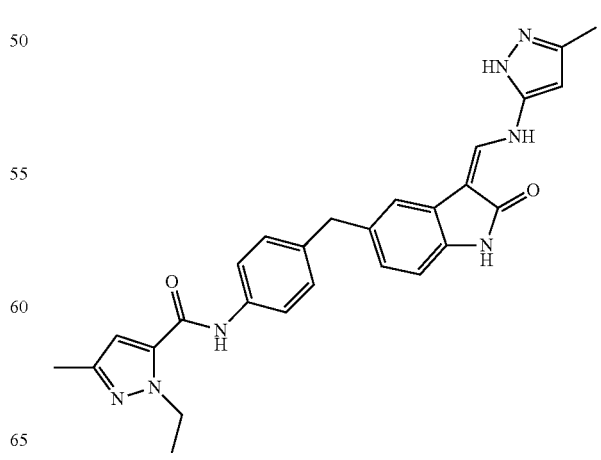

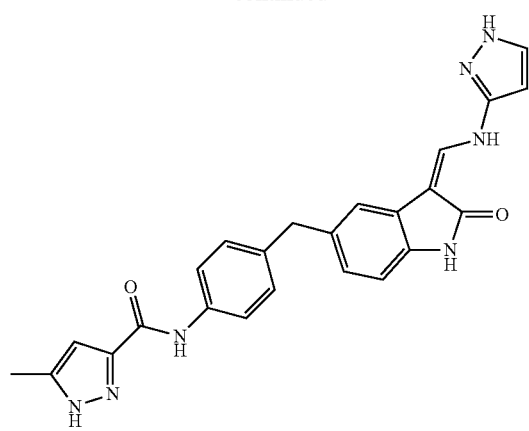
,
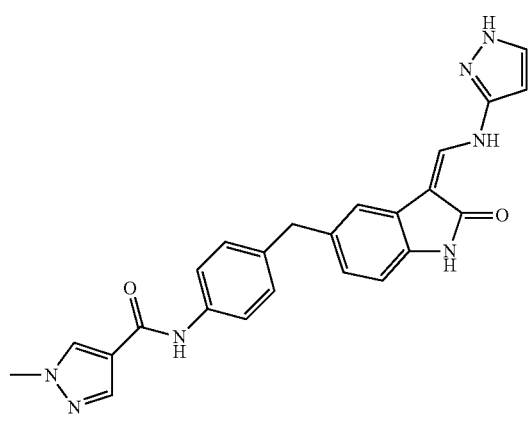
,
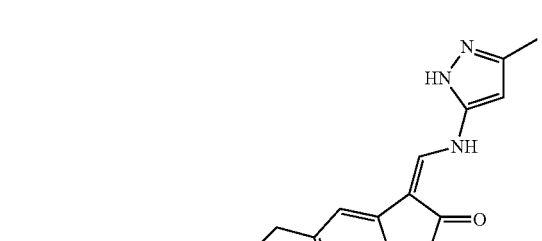
,
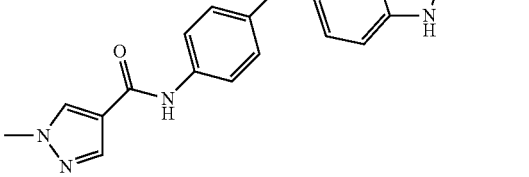
,
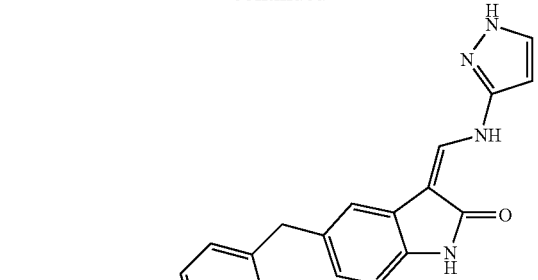
,
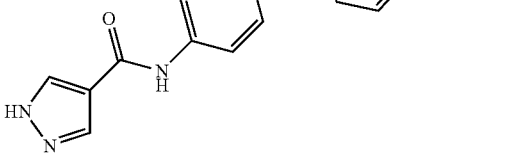
,
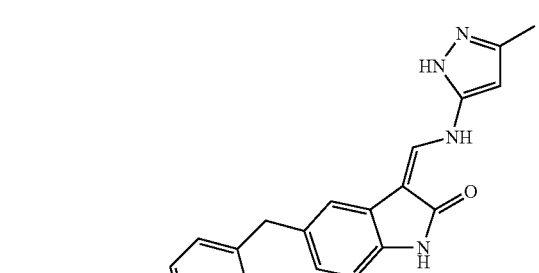
,
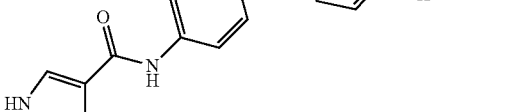
,
,
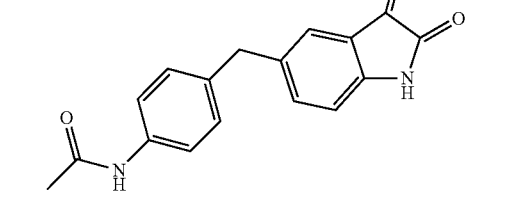
,
,

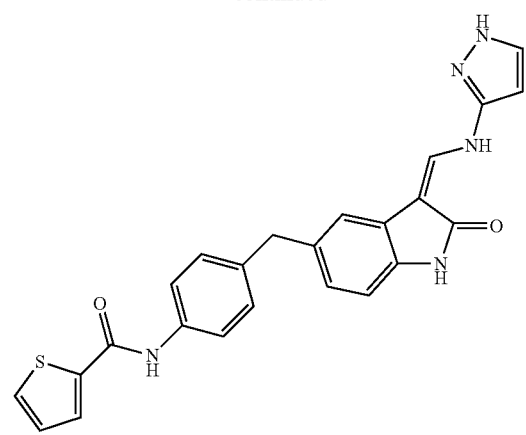
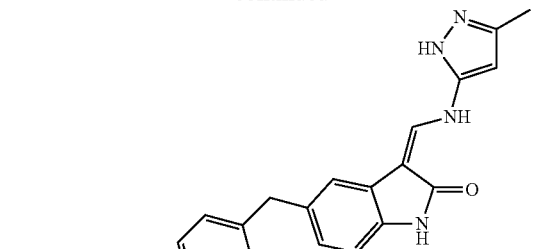
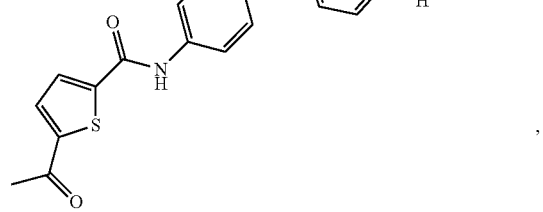
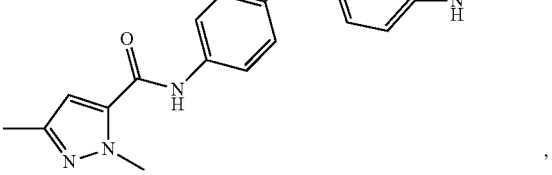
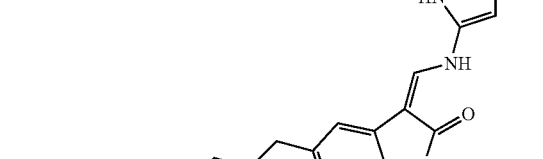
, and 47
-continued

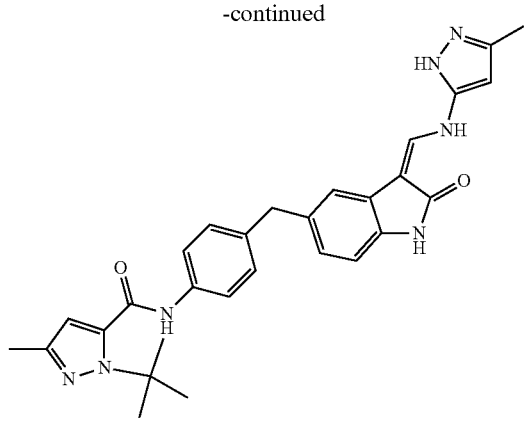

or a pharmaceutically acceptable salt thereof.

2. A compound of the formula

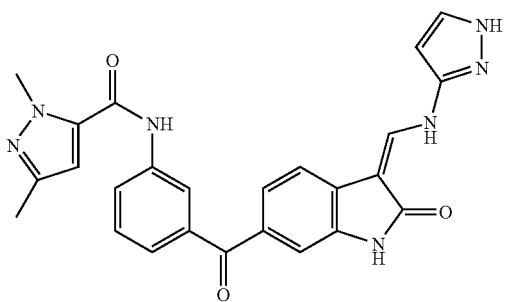 [SMILES: Cc1cc(C(=O)Nc2cccc(C(=O)c3ccc4c(c3)NC(=O)/C4=C\Nc3cc[nH]n3)c2)n(C)n1]

or a pharmaceutically acceptable salt thereof.

48

3. A compound of the formula

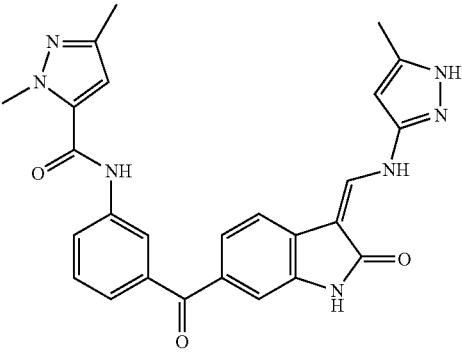 [SMILES: Cc1cc(C(=O)Nc2cccc(C(=O)c3ccc4c(c3)NC(=O)/C4=C\Nc3cc(C)[nH]n3)c2)n(C)n1]

or a pharmaceutically acceptable salt thereof.

4. A pharmaceutical composition comprising at least one compound of claim 1 or a pharmaceutically acceptable salt thereof, and at least one pharmaceutically acceptable carrier.

5. A pharmaceutical composition comprising the compound of claim 2 or a pharmaceutically acceptable salt thereof, and at least one pharmaceutically acceptable carrier.

6. A pharmaceutical composition comprising the compound of claim 3 or a pharmaceutically acceptable salt thereof, and at least one pharmaceutically acceptable carrier.

* * * * *